United States Patent
Caussil-Amblard et al.

(10) Patent No.: US 9,206,222 B2
(45) Date of Patent: Dec. 8, 2015

(54) SOLID PHASE PEPTIDE SYNTHESIS OF PEPTIDE ALCOHOLS

(75) Inventors: Muriel Caussil-Amblard, Saint Vincent de Barbeyrargues (FR); Jean Martinez, Caux (FR); Julien Tailhades, Beziers (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 628 days.

(21) Appl. No.: 13/381,310

(22) PCT Filed: Jun. 29, 2010

(86) PCT No.: PCT/EP2010/059237
§ 371 (c)(1),
(2), (4) Date: Dec. 28, 2011

(87) PCT Pub. No.: WO2011/000848
PCT Pub. Date: Jan. 6, 2011

(65) Prior Publication Data
US 2012/0108748 A1    May 3, 2012

(30) Foreign Application Priority Data
Jun. 29, 2009  (EP) .................... 09305618

(51) Int. Cl.
C07K 1/04     (2006.01)
C07K 1/06     (2006.01)
C07K 2/00     (2006.01)
C07K 7/02     (2006.01)
C07K 7/28     (2006.01)
C07K 14/655   (2006.01)

(52) U.S. Cl.
CPC ... *C07K 1/04* (2013.01); *C07K 1/06* (2013.01); *C07K 1/061* (2013.01); *C07K 1/062* (2013.01); *C07K 1/063* (2013.01); *C07K 2/00* (2013.01); *C07K 7/02* (2013.01); *C07K 7/28* (2013.01); *C07K 14/6555* (2013.01)

(58) Field of Classification Search
CPC ............ C07K 1/04; C07K 1/06; C07K 1/061; C07K 1/062; C07K 1/063; C07K 2/00; C07K 7/02; C07K 7/28
See application file for complete search history.

(56) References Cited

U.S. PATENT DOCUMENTS
4,254,023 A    3/1981  Stewart et al.

OTHER PUBLICATIONS

Isidro-Llobel et al., Chem. Rev. (2009) 109, 2455-2504.*
Spengler, Peptide Science (2007) 88(6), 823-828.*
Hsieh et al., "Dihydropyran-2-carboxylic acid, a novel bifunctional linker for the solid-phase synthesis of peptides containing a C-terminal alcohol", Chem. Commun. (1998) pp. 649-650.
Lecaillon et al., "Synthesis of cyclic peptides via O-N-acyl migration", Tetrahedron Letters, vol. 49 (2008) pp. 4674-4676.
Luis et al., "Preparation and Optimization of Polymer-Supported and Amino Alcohol Based Enantioselective Reagents and Catalysts", Ind. Eng. Chem. Res., vol. 42 (2003) pp. 5977-5982.
Mergler et al., "Solid Phase Synthesis of Fully Protected Peptide Alcohols", Tetrahedron Letters, vol. 40 (1999) pp. 4663-4664.
Sun Whang et al., "MCM-41 Supported Chiral Amino Alcohols as Enantioselective Catalysts for the Reduction of Ketones", J. Ind. Eng. Chem., vol. 8, No. 3 (2002) pp. 262-267.
Swistok et al., "A Convenient Preparation of C-Terminal Peptide Alcohols by Solid Phase Synthesis", Tetrahedron Letters, vol. 30, No. 38 (1989) pp. 5045-5048.
Tailhades et al., "Synthesis of Peptide Alcohols on the Basis of an O-N Acyl-Transfer Reaction", Angew. Chem., vol. 122 (2010) pp. 121-124.
Zeng Yan et al., "Use of Trichloroacatimidate Linker in Solid-Phase Peptide Synthesis", J. Org. Chem, vol. 68 (2003) pp. 1161-1162.

* cited by examiner

*Primary Examiner* — Karlheinz R Skowronek
*Assistant Examiner* — Catherine Mader
(74) *Attorney, Agent, or Firm* — Birch, Stewart, Kolasch & Birch, LLP

(57) ABSTRACT

The present invention relates to the synthesis of depsipeptides on solid phase support. Said depsipeptides are then implicated in a solution phase O—N acyl shift enabling to obtain the corresponding peptide alcohols.

3 Claims, 3 Drawing Sheets

SOLID PHASE PEPTIDE SYNTHESIS OF PEPTIDE ALCOHOLS

Figure 1:
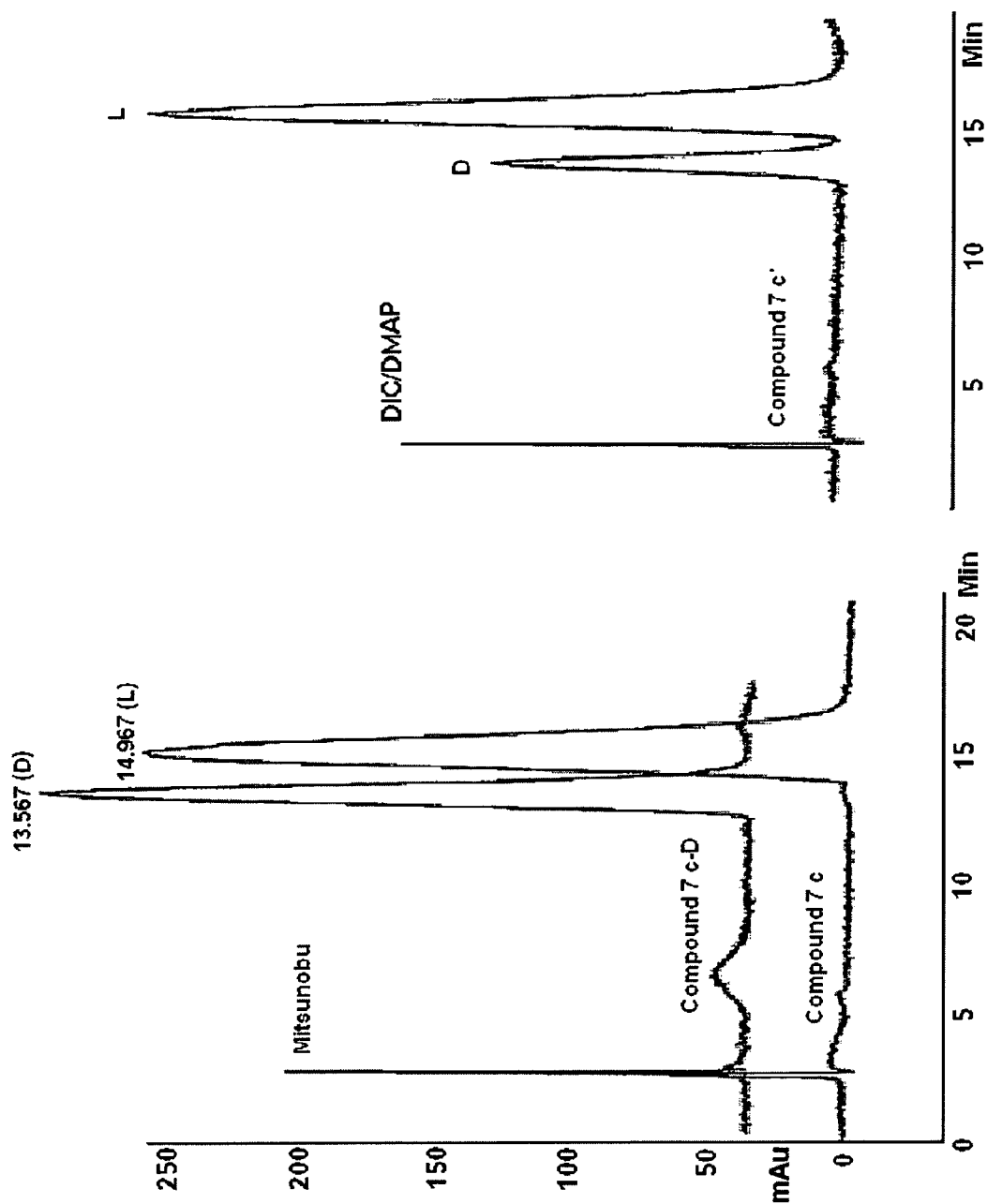

The present invention relates to a solid phase amino alcohol and its use in the synthesis of C-terminal peptide alcohols.

A peptide is an amino acid polymer wherein each amino acid is linked to its neighbor by an amide bond —CO—NH—, also called peptide bond. The number of amino acids contained in one peptide can vary from 2 to about 100, though the latter is not set precisely. Typically, both extremities of the peptide backbone finish with an amine group on one side and a carboxylic acid group on the other side. The amine extremity is referred to as the "N-terminal extremity" and the carboxylic acid extremity is referred to as the "C-terminal extremity". In the case of peptide alcohols of the present invention, a —CH$_2$—OH— group replaces the C terminal carboxylic acid. This —CH$_2$—OH is still referred to in the present invention as the "C-terminal extremity" of the peptide.

C-terminal peptide alcohols constitute an important class of compounds. They exhibit natural antibiotic properties such as peptaibols (see E. Benedetti, et Al., Proc. Natl. Acad. Sci. USA 1982, 79, 7951, W. Bauer, et Al., J. Pless, Life Sci. 1982, 31, 1133) but also potent and unique biological activity such as the metabolically stable somatostatin analog Octreotide (Sandostatin®). Other examples of peptide alcohols can be reported such as the potent enkephalin analogue Tyr-D-Ala-Gly-MePhe-Met-(O)-ol (see J. Alsina et Al., Biopolymers 2003, 71, 454), Gramicidin or Trichoderma species. In addition, peptide alcohols constitute precursor for the synthesis of peptide aldehydes, an important class of protease inhibitors and versatile synthons. —C-terminal peptide alcohols cannot be synthesized by conventional solid phase peptide synthesis (SPPS) because of the absence of a free carboxylic group to attach onto the resin. However, further SPPS methods have been developed including reductive cleavage of peptidyl ester linkage or redox-sensitive resin, ammonolytic cleavage of peptidyl ester linker with an amino alcohol and standard cleavage of peptidol-ester linker Except for chlorotrityl resin, anchoring of the hydroxyl function requires resin or C-terminal amino alcohol derivatization with a specific handle such as tetrahydropyranyl (THP)-based linkers, hemi-succinate linker, polymeric diphenyldiazomethane or the use of activated resin.

However, there is still a strong need for new methodologies for the preparation of peptide alcohols compatible with the conventional SPPS strategy using commercially standard low cost resin and affording the possibility to recover a non- or totally-protected peptide alcohol.

The first original aspect of the strategy in the present invention is the C-terminal amino alcohol residue anchored to the solid phase by its alpha-amino function rather than its less nucleophilic hydroxy function. Then, the free hydroxy function is O-acylated into a solid phase supported depsipeptide, which is then used in a conventional SPPS. At the end of the solid phase synthesis, cleavage releases an unprotected or protected depsipeptide. N.B.: Some of the results described in the present application have also been reported in a scientific article: J. Tailhades et al., "Synthesis of peptide alcohols on the basis of an O—N Acyl-Transfert Reaction", Angew. Chem., 2010, 122, pp 121-124 (and supporting information).

A depsipeptide is a peptide wherein one or more of the amide —CO—NHR— bonds have been replaced by an ester —CO—OR bond. As at least one of the peptide bond has been modified, these peptides are comprised in a broader family of molecules called pseudopeptides.

To restore the native peptide alcohols, the key step of the synthesis consists in an O—N-acyl intramolecular transfer on the C-terminal amino alcohol which is used as a "switch" or "click" element (see synthesis Scheme 7 in the examples). This O—N-acyl intramolecular transfer method has been the subject of extensive studies but it has never been applied to the synthesis of peptide alcohols starting from amino alcohols derived from amino acids.

In a first aspect, the present invention relates to a solid phase amino alcohol having the following formula (I):

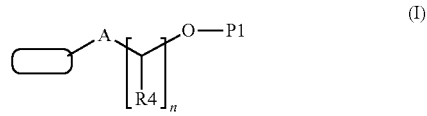

wherein, ▭ represents a solid support appropriate for peptide synthesis, the fragment A represents the amine-C$_\alpha$(residue)- of an amino acid chosen in the group of natural or unnatural amino acids.

"Natural amino acid" means the natural occurring form, i.e. the L form (except for glycine), of glycine (Gly), alanine (Ala), valine (Val), leucine (Leu), isoleucine (Ile), serine (Ser), threonine (Thr), phenylalanine (Phe), tyrosine (Tyr), tryptophan (Trp), cysteine (Cys), methionine (Met), proline (Pro), hydroxyproline, aspartic acid (Asp), asparagine (Asn), glutamine (Gln), glutamic acid (Glu), histidine (His), arginine (Arg), ornithine, and lysine (Lys).

Hence, "proteogenic" and 'natural' amino acids have the same meaning

Unnatural amino acids comprise for example all natural amino acids defined as above, in their D form.

Unnatural amino acids also comprise natural amino acids defined as above wherein, naturally-occurring amino acids include a heteroatom-containing functional group, e.g., an alcohol (serine, tyrosine, hydroxyproline and threonine), an amine (lysine, ornithine, histidine and arginine), a thiol (cysteine) or a carboxylic acid (aspartic acid and glutamic acid) wherein the heteroatom-containing functional group is modified to include a protecting group. The side-chain is then referred to as the "protected side-chain" of an amino acid.

"Side chain of an amino acid" means the moiety which substitutes the α-carbon of an amino acid. The α-carbon refers to the carbon in a position of the carboxylic acid of an amino acid. For example, α-carbon side chains of naturally occurring α-amino acids such as glycine, valine, alanine, and aspartic acid include the hydrogen atom, isopropyl, methyl, and —CH$_2$COOH respectively.

For example, in an Fmoc synthesis strategy, side chains of natural amino acids may be protected with standard protecting groups such as t-butyl (t-Bu), trityl (Trt) and t-butyloxycarbonyl (Boc). The t-Bu group is the preferred side-chain protecting group for amino acid residues tyrosine (Tyr), threonine (Thr), serine (Ser), glutamic acid (Glu) and aspartic acid (Asp); the Trt group is the preferred side-chain protecting group for amino acid residues histidine (His), glutamine (Gln) and asparagine (Asn); and the Boc group is the preferred side-chain protecting group for amino acid residues lysine (Lys) and tryptophane (Trp).

For example, in a Boc synthesis strategy, side chains of natural amino acids may be protected with standard protecting groups such as benzyls ethers or esters or NO$_2$ for the arginine side chain, for example. These strategies and the carrying out of these strategies are well known by the skilled person in the art, and can be found in peptide synthesis dedicated books such as: Paul Lloyd-Williams, Fernando Albericio, Ernest Giralt, Chemical Approaches to the Synthesis of Peptides and Proteins, CRC Press, 1997 or Houben-Weyl Methods of Organic Chemistry, Synthesis of Peptides and Peptidomimetics, Vol E 22a, Vol E 22b, Vol E 22c, Vol E 22d., M. Goodmann Ed., Georg Thieme Verlag, 2002.

However, it is not necessary to protect the side-chain of glycine, alanine, valine, leucine, isoleucine, phenylalanine, methionine and proline.

Unnatural amino acids also comprise for example, β-alanine, allylglycine, tert-leucine, norleucine (Nle), 3-aminoadipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-amino cyclo hexaneacetic acid, 1-amino-1-cyclohexanecarboxylic acid, (1R,2R)-2-aminocyclohexanecarboxylic acid, (1R,2S)-2-amino cyclo hexane carboxylic acid, (1S,2R)-2-amino cyclo hexanecarboxylic acid, (1S,2S)-2-aminocyclohexanecarboxylic acid, 3-aminocyclohexanecarboxylic acid, 4-aminocyclohexanecarboxylic acid, (1R,2R)-2-aminocyclopentanecarboxylic acid, (1R,2S)-2-aminocyclopentanecarboxylic acid 1-amino-1-cyclopentanecarboxylic acid, 1-amino-1-cyclopropanecarboxylic acid, 3-aminomethylbenzoic acid, 4-aminomethylbenzoic acid, 2-aminobutanoic acid, 4-aminobutanoic acid, 6-aminohexanoic acid, 1-amino indane-1-carboxylic acid, 2-Amino iso butyric acid (Aib), 4-aminomethyl-phenylacetic acid, 4-aminophenylacetic acid, 3-amino-2-naphthoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hyroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-aminopyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, tert-butylglycine, γ-carboxyglutamate, β-cyclohexylalanine, citruline, 2,3-diamino propionic acid, hippuric acid, homocyclohexylalanine, moleucine, homophenylalanine, 4-hydroxyproline, indoline-2-carboxylic acid, isonipecotic acid, α-methyl-alanine, naphtyl-alanine, nicopetic acid, norvaline, octahydroindole-2-carboxylic acid, ornithine, penicillamine, phenylglycine (Phg), 4-phenyl-pyrrolidine-2-carboxylic acid, propargylglycine, 3-pyridinylalanine, 4-pyridinylalanine, 1-pyrrolidine-3-carboxylic acid, sarcosine, the statins, tetrahydroisoquinoline-1-carboxylic acid, 1,2,3,4-tetrahydroisoquinoline-3-carboxylic acid, tranexamic acid, 4,4-difluoro proline, 4-fluoro proline, alpha-(3,4-difluorobenzyl)-proline, gamma-(3,4-difluorobenzyl)-proline, alpha-(trifluoromethyl)phenylalanine, hexafluoroleucine, 5,5,5-trifluoroleucine, 6,6,6-trifluoronorleucine, 2-(trifluoromethyl)leucine, 2-(trifluoromethyl)norleucine, 4,4,4-trifluorovaline, 4,4,4',4',4'-hexafluorovaline, pentafluorophenylalanine, 2,3-difluorophenylalanine, 2,4-difluorophenylalanine, 2,5-difluorophenylalanine, 2,6-difluorophenylalanine, 3,4-difluorophenylalanine, 3,5-difluorophenylalanine, 3,3-difluoro-3-(4-fluorophenyl) alanine, 2,3-difluorophenylglycine, 2,4-difluorophenylglycine, 2,5-difluorophenylglycine, 3,4-difluorophenylglycine, 4,4-difluoroethylglycine, 4,4,4-trifluoroethylglycine and hexafluoronorleucine, and the like.

Each R4 independently represents a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, a —($C_1$-$C_{10}$ alkyl)-($C_4$-$C_{12}$) monocyclic or polycyclic unsaturated hydrocarbonated group, said groups being non substituted or substituted by 1 to 10 fluorine atoms, 1 to 5-NRR', 1 to 5SH, 1 to 5OR, 1 to 5COR, 1 to 5COOR, 1 to 5CONRR', 1 to 5NHCONH$_2$, and/or 1 to 5NHC(NH)NH$_2$ moieties wherein R and R' independently from one another represent a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, a —($C_1$-$C_{10}$ alkyl)-($C_4$-$C_{12}$) monocyclic or polycyclic unsaturated hydrocarbonated group, wherein the NH$_2$, NH, COOH, SH and OH functions of these groups are advantageously protected by one or several identical or different O-protecting and/or N-protecting and/or S-protecting groups or atoms. Advantageously R4 represents a hydrogen atom, a $C_1$-$C_6$ alkyl group, a $C_2$-$C_6$ alkenyl group, or a —($C_1$-$C_6$ alkyl)-aryl group.

More advantageously, R4 represents a hydrogen atom.

P1 represents a hydrogen atom or an O-protecting group.

Advantageously, P1 represents a hydrogen atom.

n is an integer from 1 to 10.

Advantageously, n is equal to 1.

In the case of n>1, each R4 can form with another R4 and with the atoms which carry them a cyclic or polycyclic moiety wherein each ring is a 3- to 10-membered ring, saturated or unsaturated, hydrocarbonated or heterocyclic, the number of rings being comprised between 1 and 5, non substituted or substituted by 1 to 10 fluorine atoms, 1 to 5-NRR', 1 to 5SH, 1 to 5OR, 1 to 5COR, 1 to 5COOR, 1 to 5CONRR', 1 to 5NHCONH$_2$, and/or 1 to 5NHC(NH)NH$_2$ moieties wherein R and R' independently represent from one another a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, or a —($C_1$-$C_{10}$ alkyl)-($C_4$-$C_{12}$) monocyclic or polycyclic unsaturated hydrocarbonated group, wherein the NH$_2$, NH, COOH, SH and OH functions of these groups are advantageously protected by one or several identical or different O-protecting and/or N-protecting and/or S-protecting groups or atoms.

However, solid supported amino alcohols have been described in a totally different application (catalysis) in the following documents: S. V. Luis et al., *Ind. Eng. Chem. Res.* 2003, 42, 5977-5982, and M. S. Whang et al., *J. Ind. Eng. Chem.* 2002, 8, 262-267. Therefore, the following solid supported amino alcohols have previously been described when for the following solid phase amino alcohols of formulas Ia, Ib, Ic, Id, Ie, If:

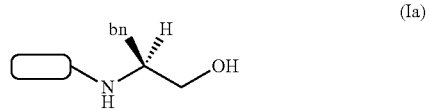

(Ia)

wherein the solid phase support is a Merrifield's resin or a chlorosulfonated polymer or a MCM-41 mesoporous material or silica gel,

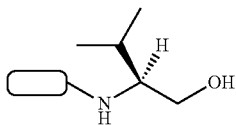
(Ib)

wherein the solid phase support is a Merrifield's resin or a chlorosulfonated polymer or a MCM-41 mesoporous material or silica gel,

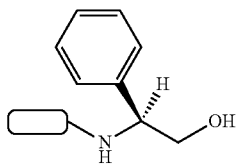
(Ic)

wherein the solid phase support is a Merrifield's resin or a chlorosulfonated polymer or a MCM-41 mesoporous material or silica gel,

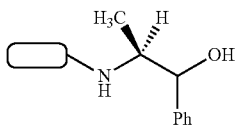
(Id)

wherein the solid phase support is a Merrifield's resin or a chlorosulfonated polymer or a MCM-41 mesoporous material or silica gel,

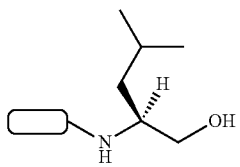
(Ie)

wherein the solid phase support is a Merrifield's resin or a chlorosulfonated polymer,

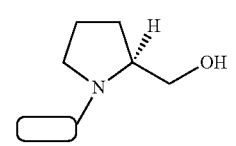
(If)

wherein the solid phase support is a Merrifield's resin.

Within the framework of the present invention, "($C_1$-$C_6$) alkyl" means any linear saturated hydrocarbon radical from one to six carbon atoms or ($C_3$-$C_6$) branched saturated hydrocarbon radical. Examples of ($C_1$-$C_6$) alkyl radicals include, but are not limited to, methyl, ethyl, n-propyl, isopropyl, 1-ethylpropyl, sec-butyl, iso-butyl, tert-butyl, n-butyl, n-pentyl, n-hexyl, etc.

Within the framework of the present invention, "($C_1$-$C_6$) linear alkyl group" means any linear saturated hydrocarbon radical having from one to six carbon atoms. Examples of linear ($C_1$-$C_6$) alkyl radicals consist in methyl, ethyl, n-propyl, n-butyl, n-pentyl, n-hexyl.

Within the framework of the present invention, "($C_3$-$C_6$) branched alkyl group" means any branched saturated hydrocarbon radical having from three to six carbon atoms.

Examples of branched ($C_3$-$C_6$) alkyl radicals include, but are not limited to, isopropyl, 1-ethylpropyl, sec-butyl, ter-butyl etc.

Within the framework of the present invention, "($C_2$-$C_6$) alkenyl group" means any linear or ($C_3$-$C_6$) branched hydrocarbon alkenyl radical having from two to six carbon atoms and at least one unsaturation between two carbon atoms. Examples of ($C_2$-$C_6$) alkenyl radicals include, but are not limited to, ethylene, propenyl, butenyl, pentenyl, etc.

Within the framework of the present invention, "($C_2$-$C_6$) linear alkenyl group" means any linear hydrocarbon radical having from two to six carbon atoms and at least one unsaturation between two carbon atoms. Examples of ($C_2$-$C_6$) linear alkenyl radicals consist in ethenyl, n-propenyl, n-butenyl, n-pentenyl, n-hexenyl.

Within the framework of the present invention, "branched ($C_2$-$C_6$) alkenyl group" means any branched hydrocarbon radical having from two to six carbon atoms and at least one unsaturation between two carbon atoms. Examples of branched ($C_2$-$C_6$) alkenyl radicals include, but are not limited to isopropenyl, isobutenyl, sec-butenyl, isopentenyl, etc.

Within the framework of the present invention, "($C_2$-$C_6$) alkynyl group" means any linear or ($C_3$-$C_6$) branched hydrocarbon alkynyl radical having from two to six carbon atoms and at least one triple bond between the two carbon atoms. Examples of ($C_2$-$C_6$) alkynyl radicals include, but are not limited to, ethynyl, propargyl, butynyl, pentynyl, etc.

Within the framework of the present invention, "($C_2$-$C_6$) linear alkynyl group" means any linear hydrocarbon radical having from two to six carbon atoms and at least one triple bond between two carbon atoms. Examples of ($C_2$-$C_6$) linear alkynyl radicals consist in ethynyl, n-propynyl, n-butynyl, n-pentynyl, n-hexynyl.

Within the framework of the present invention, "branched ($C_2$-$C_6$) alkynyl group" means any branched hydrocarbon radical having from two to six carbon atoms and at least one triple bond between two carbon atoms. Examples of branched ($C_2$-$C_6$) alkynyl radicals include, but are not limited to isobutynyl, sec-butynyl, isopentenyl, etc. Within the framework of the present invention, a ($C_4$-$C_{12}$) monocyclic or polycyclic saturated hydrocarbonated group refers indifferently in the present invention to a saturated hydrocarbonated group consisting of one or more cycles, advantageously 1, 2, 3, 4, 5 or 6 cycles, advantageously 1, 2 or 3 cycles, each cycle being a 4-, 5-, 6- or 7-membered cycle, more advantageously a 5-, or 6-membered cycle.

Within the framework of the present invention, a ($C_4$-$C_{12}$) monocyclic or polycyclic unsaturated hydrocarbonated group refers indifferently in the present invention to a unsaturated hydrocarbonated group consisting of one or more cycles, advantageously 1, 2, 3, 4, 5 or 6 cycles, advantageously 1, 2 or 3 cycles, each cycle being a 4-, 5-, 6- or 7-membered cycle, more advantageously a 5-, or 6-membered cycle. Furthermore, the ($C_4$-$C_{12}$) monocyclic or polycyclic unsaturated hydrocarbonated group may in addition refer to aromatic or partially saturated hydrocarbonated groups, such as for example monocyclic or polycyclic unsaturated hydrocarbonated groups in which respectively the cycle or at least one cycle of the polycyclic unsaturated hydrocarbonated group, advantageously all the cycles of the polycyclic unsaturated hydrocarbonated group, are aryl cycles.

It should be also understood that in the case where the polycyclic group consists in 2 cycles, said cycles may be fused or bridged together, or can be linked together by a spiro junction, or that a carbon atom of one cycle of the ($C_4$-$C_{12}$) polycyclic hydrocarbonated group forms a covalent bound with a carbon atom of another cycle of the ($C_4$-$C_{12}$) polycyclic hydrocarbonated group.

For example, a bicyclic hydrocarbonated group in which each cycle is a 6-membered cycle can be:

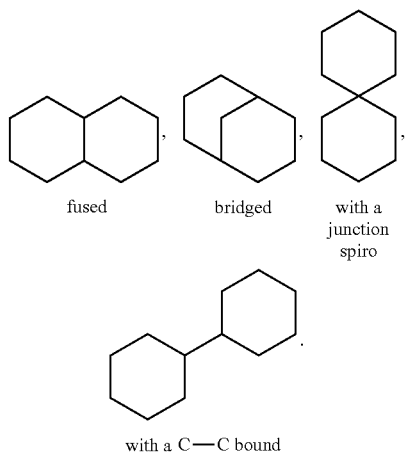

In the case where the polycyclic group consists in more than 2 cycles, the skilled person will understand that there may be a combination of these cycle configurations.

It should be also understood that one or more of said cycles of the ($C_4$-$C_{12}$) monocyclic or polycyclic saturated or unsaturated hydrocarbonated group may be an heterocycle, which means that said cycles incorporate one or more, advantageously one or two heteroatoms (selected advantageously from nitrogen, oxygen or sulfur atom).

Other examples of ($C_4$-$C_{12}$) monocyclic or polycyclic saturated hydrocarbonated group include cyclopentyl, cyclohexyl, cycloheptyl, adamantly, piperidinyl or norbornyl group. Advantageously, ($C_4$-$C_{12}$) monocyclic or polycyclic saturated hydrocarbonated group is a ($C_5$-$C_{10}$) monocyclic or polycyclic saturated hydrocarbonated group, more advantageously a $C_5$ or $C_6$ monocyclic or polycyclic saturated hydrocarbonated group. More advantageously, the ($C_4$-$C_{12}$) monocyclic or polycyclic saturated hydrocarbonated group is a cyclopentyl, cyclohexyl, adamantly, piperidinyl, or norbornyl group.

Other examples of ($C_4$-$C_{12}$) monocyclic or polycyclic unsaturated hydrocarbonated group include phenyl, naphtyl, pyridinyl, imidazolyl or indolyl group.

"($C_1$-$C_6$ alkyl)-($C_4$-$C_{12}$) monocyclic or polycyclic saturated hydrocarbonated group" means any ($C_4$-$C_{12}$) monocyclic or polycyclic saturated hydrocarbonated group such as defined above, linked to the rest of the molecule by the means of a ($C_1$-$C_6$) alkyl group such as defined above.

"($C_1$-$C_6$ alkyl)-($C_4$-$C_{12}$) monocyclic or polycyclic unsaturated hydrocarbonated group" means any ($C_4$-$C_{12}$) monocyclic or polycyclic unsaturated hydrocarbonated group such as defined above, linked to the rest of the molecule by the means of a ($C_1$-$C_6$) alkyl group such as defined above.

"Aryl" means an aromatic group such as a phenyl, naphtyl or pyridinyl group.

"—($C_1$-$C_{10}$ alkyl)-aryl" means an alkyl group containing 1 to 10 carbons substituted by an aryl radical. Preferred alkylaryl groups include benzyl, naphth-1-ylmethyl naphth-2-ylmethyl, and phenethyl.

"Azacycloalkane" means a saturated aliphatic ring containing a nitrogen atom. Preferred azacycloalkanes include pyrollidine and piperidine During the preparation of compounds of the present invention, or intermediates thereto, it may also be desirable or necessary to prevent cross-reaction between chemically active substituents other than those present on naturally occurring or other amino acids. The substituents may be protected by standard blocking groups which may subsequently be removed or retained, as required, by known methods to afford the desired products or intermediates. Selective protection or deprotection may also be necessary or desirable to allow conversion or removal of existing substituents, or to allow subsequent reaction to afford the final desired product.

The selection of a suitable protecting group depends upon the functional group being protected, the conditions to which the protecting group is being exposed and to other functional groups which may be present in the molecule.

Suitable protecting groups for the functional groups discussed above are described in Greene and Wuts, "Protective Groups in Organic Synthesis", John Wiley & Sons (1991), the entire teachings of which are incorporated into this application by reference as if fully set forth herein. The skilled artisan can select, using no more than routine experimentation, suitable protecting groups for use in the disclosed synthesis, including protecting groups other than those described below, as well as conditions for applying and removing the protecting groups.

"N-protecting group" means a substituent such as the N-protecting groups disclosed in Greene, "Protective Groups in Organic Synthesis", Wiley, New York, 2007 4$^{th}$ edition; Harrison et al. "Compendium of Synthetic Organic Methods", Vol. 1 to 8 (J. Wiley & sons, 1971 to 1996); Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol E 22a, Vol E 22b, Vol E 22c, Vol E 22d., M. Goodmann Ed., Georg Thieme Verlag, 2002, which protects the nitrogen against undesirable reactions. "N-protecting group" can comprise carbamates, amides, N-alkylated derivatives, amino acetal derivatives, N-benzylated derivatives, imine derivatives, enamine derivatives, and N-heteroatom derivatives. For example, N-protecting groups comprise the formyl group, acetyl group, benzoyl group, pivaloyl group, phenylsulfonyl group, benzyl (Bn) group, t-butyloxycarbonyl (Boc) group, benzyloxycarbonyl (Cbz) group, p-methoxybenzylo xycarbonyl group, p-nitrobenzyl-oxycarbonyl group, trichloroethoxycarbonyl (troc) group, allyloxycarbonyl (alloc) group, 9-fluorenylmethoxycarbonyl (Fmoc) group, trifluoroacetyl group, benzyle (substituted or not) carbamate groups, p-methoxy-benzyloxycarbonyl group, and the like.

"O-protecting group" means a substituent such as the O-protecting groups disclosed in Greene, "Protective Groups in Organic Synthesis", Wiley, New York, 2007 4$^{th}$ edition and Harrison et al. "Compendium of Synthetic Organic Methods", Vol. 1 to 8 (J. Wiley & sons, 1971 to 1996); Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol E 22a, Vol E 22b, Vol E 22c, Vol E 22d., M. Goodmann Ed., Georg Thieme Verlag, 2002, which protects reactive oxygen against undesirable reactions. The "O" of "O-protecting group" can be for example the oxygen in the OH of an alcohol, the oxygen in the OH of a carboxylic acid, the oxygen in the C=O of a ketone.

In the case of the OH of an alcohol, the "O-protecting group" can comprise for example methyl ethers or branched or straight alkyl ethers such as methoxymethyl ethers, benzylo xymethyl ethers, 2-methoxyethoxymethyl ethers, 2-(trimethylsilyl)ethoxymethyl ethers, t-butyl ethers (-OtBu), benzyl ethers (OBz), triphenylmethyl, substituted benzyl ethers, tetrahydropyranyl ethers, allyl ethers, substituted ethyl ethers, for example, 2,2,2-trichloroethyl, silyl ethers or alkylsilyl ethers, for example trimethylsilyl ethers, t-butyldimethylsilyl ethers and t-butyldiphenylsilyl ethers, heterocycle ethers; 4,4'-dimethoxybenzhydryl (Mbh) group, a trityl group (hereinafter referred to as "Trt") as a protecting group for w-carbamido group of Gln or Asn; an OBzl group, an OtBu group as the protecting group for a free hydroxyl group; in the case of the OH of a carboxylic acid, the "O-protecting group" can form with the acid an ester function, for example, tert-butyl esters (CO—OtBu), benzyl esters (CO—OBz), methyl esters (CO—OMe), phenacyloxy ester (CO—OPac) or silyl esters, and the like.

"S-protecting group" means a substituent such as the S-protecting groups disclosed in Greene, "Protective Groups in Organic Synthesis", Wiley, New York, 2007 4$^{th}$ edition Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol E 22a, Vol E 22b, Vol E 22c, Vol E 22d., M. Goodmann Ed., Georg Thieme Verlag, 2002, which protects reactive sulphur against undesirable reactions.

"S-protecting group" can comprise the benzyl group, a Trt group, acetamidomethyl, the S-tert-butyl, S-acetyl, S-methoxymethyl, as the protecting group for a free mercapto group in the amino acid residue and the like.

The A fragment represents the following formula (I'):

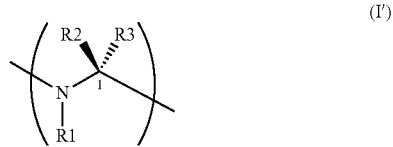

wherein

R1 represents a hydrogen atom, a $C_1$-$C_6$ alkyl group, a $C_2$-$C_6$ alkenyl group, a $C_2$-$C_6$ alkynyl group, a $(C_4$-$C_{12})$ monocyclic or polycyclic saturated hydrocarbonated group, a —$(C_1$-$C_{10}$ alkyl)-$(C_4$-$C_{12})$ monocyclic or polycyclic saturated hydrocarbonated group, a $(C_4$-$C_{12})$ monocyclic or polycyclic unsaturated hydrocarbonated group, a —$(C_1$-$C_{10}$ alkyl)-$(C_4$-$C_{12})$ monocyclic or polycyclic unsaturated hydrocarbonated group, or a CO—R group, wherein R represents a hydrogen, a $C_1$-$C_6$ alkyl group, a $C_2$-$C_6$ alkenyl group, a $C_2$-$C_{10}$ alkynyl group, a $(C_4$-$C_{12})$ monocyclic or polycyclic saturated hydrocarbonated group, a —$(C_1$-$C_{10}$ alkyl)-$(C_4$-$C_{12})$ monocyclic or polycyclic saturated hydrocarbonated group, a $(C_4$-$C_{12})$ monocyclic or polycyclic unsaturated hydrocarbonated group, or a —$(C_1$-$C_{10}$ alkyl)-$(C_4$-$C_{12})$ monocyclic or polycyclic unsaturated hydrocarbonated group.

Advantageously, R1 represents a hydrogen atom, a $C_1$-$C_6$ alkyl group, a $C_2$-$C_6$ alkenyl group, or a —$(C_1$-$C_6$ alkyl)-aryl group.

More advantageously, R1 represents a hydrogen atom or a $C_1$-$C_6$ alkyl group.

R2 and R3 independently represent a hydrogen atom, a fluorine atom, a $C_1$-$C_{20}$ alkyl group, a $C_2$-$C_{10}$ alkenyl group, a $(C_4$-$C_{12})$ monocyclic or polycyclic saturated hydrocarbonated group, a —$(C_1$-$C_{10}$ alkyl)-$(C_4$-$C_{12})$ monocyclic or polycyclic saturated hydrocarbonated group, a $(C_4$-$C_{12})$ monocyclic or polycyclic unsaturated hydrocarbonated group, a —$(C_1$-$C_{10}$ alkyl)-$(C_4$-$C_{12})$ monocyclic or polycyclic unsaturated hydrocarbonated group, a —$(C_1$-$C_{10}$ alkyl)-S—$(C_1$-$C_{10}$ alkyl) group, a —$(C_1$-$C_{10}$ alkyl)-indol-2-yl group, —a $(C_1$-$C_{10}$ alkyl)-imidazolyl group, said groups being non substituted or substituted by 1 to 10 fluorine atoms, 1 to 5-NRR', 1 to 5SH, 1 to 5OR, 1 to 5COR, 1 to 5COOR, 1 to 5CONRR', 1 to 5NHCONH$_2$, and/or 1 to 5NHC(NH)NH$_2$ moieties wherein R and R' independently represent from one another a hydrogen atom, a $C_1$-$C_6$ alkyl group, a $C_2$-$C_6$ alkenyl group, a $C_2$-$C_{10}$ alkynyl group, a $(C_4$-$C_{12})$ monocyclic or polycyclic saturated hydrocarbonated group, a —$(C_1$-$C_{10}$ alkyl)-$(C_4$-$C_{12})$ monocyclic or polycyclic saturated hydrocarbonated group, a $(C_4$-$C_{12})$ monocyclic or polycyclic unsaturated hydrocarbonated group, or a —$(C_1$-$C_{10}$ alkyl)-$(C_4$-$C_{12})$ monocyclic or polycyclic unsaturated hydrocarbonated group, wherein the NH$_2$, NH, COOH, SH and OH functions of these groups are advantageously protected by one or several identical or different O-protecting and/or N-protecting and/or S-protecting groups or atoms.

Advantageously, R1, R2 and/or R3 independently are side chains of natural or unnatural amino acids.

More advantageously, R1, R2 and/or R3 independently are side chains of natural amino acids.

Even more advantageously, R2 and/or R3 independently are side chains of natural or unnatural amino acids.

Most advantageously, R2 and/or R3 independently are side chains of natural amino acids.

In the case of proline, R1 and R2 or R1 and R3 form together with the atoms which carry them a 5-membered azacycloalkane ring.

Advantageously, R2 and R3 independently represent a hydrogen atom, a $C_1$-$C_{20}$ alkyl group, a $C_2$-$C_{10}$ alkenyl group, a —$(C_1$-$C_{10}$ alkyl)-aryl group, a —$C_1$-$C_{10}$ alkyl-OH group, a —$C_1$-$C_{10}$ alkyl-SH group, a —$(C_1$-$C_{10}$ alkyl)-S—$(C_1$-$C_{10}$ alkyl) group, a —$(C_1$-$C_{10}$ alkyl)-indol-2-yl group, a —$(C_1$-$C_{10}$ alkyl)-phenol group, a —$(C_1$-$C_{10}$ alkyl)-CONH$_2$ group, a —$(C_1$-$C_{10}$ alkyl)-imidazolyl group, a —$(C_1$-$C_{10}$ alkyl)-COOH group, a —$C_1$-$C_{10}$ alkyl-NH$_2$ group, a —$(C_1$-$C_{10}$ alkyl)-NHC(NH)NH$_2$ group, the NH$_2$, NH, COOH, SH and OH functions of these groups being advantageously protected by one or several identical or different O-protecting and/or N-protecting and/or S-protecting groups or atoms.

More advantageously, R2 and R3 independently represent a hydrogen atom, a CH$_3$ group, a —CH(CH$_3$)$_2$ group, a —CH(CH$_3$)—CH$_2$CH$_3$ group, a —CH$_2$CH(CH$_3$)$_2$ group, a benzyl group, a —CH$_2$—OH group, a —CH(OH)—CH$_3$ group, a —CH$_2$—SH group, a —(CH$_2$)$_2$—S—CH$_3$ group, a —CH$_2$-indol-2-yl group, a —CH$_2$-phenol group, a —CH$_2$—CONH$_2$ group, a —(CH$_2$)$_2$—CONH$_2$ group, a —CH$_2$-imidazolyl group, a —CH$_2$—COOH group, a —(CH$_2$)-2—COOH group, a —(CH$_2$)$_4$—NH$_2$ group, a —(CH$_2$)$_3$—NHC(NH)NH$_2$ group, the NH$_2$, NH, COOH, SH and OH functions of these groups being advantageously protected by one or several identical or different O-protecting and/or N-protecting and/or S-protecting groups or atoms.

R1 and R2, and/or R1 and R3 can form together with the atoms which carry them a monocyclic or polycyclic moiety wherein each ring is a 3- to 10-membered hydrocarbonated ring, saturated or unsaturated, the number of rings being comprised between 1 and 5, non substituted or substituted by 1 to 10 fluorine atoms, 1 to 5-NRR', 1 to 5SH, 1 to 5OR, 1 to 5COR, 1 to 5COOR, 1 to 5CONRR', 1 to 5NHCONH$_2$, and/or 1 to 5NHC(NH)NH$_2$ moieties wherein R and R' independently represent from one another a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, or a —($C_1$-$C_{10}$ alkyl)-($C_4$-$C_{12}$) monocyclic or polycyclic unsaturated hydrocarbonated group, wherein the NH$_2$, NH, COOH, SH and OH functions of these groups are advantageously protected by one or several identical or different O-protecting and/or N-protecting and/or S-protecting groups or atoms.

Advantageously, R1 and R2 and/or R1 and R3 can form together with the atoms which carry them a 4- to 10-membered azacycloalkane ring.

Even more advantageously, R1 and R2 or R1 and R3 can form together with the atoms which carry them a 5-membered azacycloalkane ring.

When R2 and/or R3 are side chains of natural amino acids, the R2 and/or R3 residues may or may not be protected with standard protecting groups such as t-butyl (t-Bu), trityl (trt), benzyl (Bn or Bzl) and t-butyloxycarbonyl (Boc).

For example, in an Fmoc synthesis strategy, the t-Bu group is the preferred side-chain protecting group for amino acid residues tyrosine (Tyr), threonine (Thr), serine (Ser), glutamic acid (Glu) and aspartic acid (Asp); the Trt group is the preferred side-chain protecting group for amino acid residues histidine (His), glutamine (Gln) and asparagine (Asn); and the Boc group is the preferred side-chain protecting group for amino acid residues lysine (Lys) and tryptophane (Trp).

In a Boc synthesis strategy, side chains of natural amino acids may be protected with standard protecting groups such as benzyls ethers or esters or NO$_2$ for the arginine side chain, for example. These strategies and the carrying out of these strategies are well known by the skilled person in the art, and can be found in peptide synthesis dedicated books such as: Paul Lloyd-Williams, Fernando Albericio, Ernest Giralt, Chemical Approaches to the Synthesis of Peptides and Proteins, CRC Press, 1997 or Houben-Weyl Methods of Organic Chemistry, Synthesis of Peptides and Peptidomimetics, Vol E 22a, Vol E 22b, Vol E 22c, Vol E 22d., M. Goodmann Ed., Georg Thieme Verlag, 2002.

However, it is not necessary to protect the side-chain of glycine, alanine, valine, leucine, isoleucine, phenylalanine, methionine and proline.

In formula (I'), the carbon to which is linked R2 is referred to as "$C_1$".

The carbon $C_1$ has an (S) or (R) configuration when $C_1$ is an asymmetrical carbon.

The terms "solid support", "solid phase" and "resin", refer indifferently in the present invention to a support conventionally used in organic chemistry, and particularly in peptide synthesis comprising a matrix polymer and a linker The solid support comprises a base matrix such as gelatinous or macroporous resins, for example polystyrene, and an anchor referred to as a "linker" designed to produce after cleavage a given functionality (i.e. amines in the present case) or a family of related functional groups. The name of the solid support, in all strictness, refers to the name of the linker and the matrix (for example Rink amide AMPS signifying 4-[2', 4'-dimethoxyphenyl-(9-fluoromethyloxycarbonyl)amino methyl]phenoxy-aminomethyl PS in the case of Rink resin).

Advantageously the base support is chosen among the polystyrene supports, polyamide supports, polyethylene glycol supports, polyacrylic supports, composite supports and copolymers thereof, such as polyacrylic/beta-alanine copolymer supports, polyacrylamide/polystyrene copolymer supports, polyacrylamide/polethylene glycol copolymer supports and polyethyleneglycol/polystyrene copolymer supports, it being possible for said support to be in the form of beads, of a film-coated support such as rings or lanterns, of a plug, or of a non-cross-linked soluble support.

More advantageously, the base support is selected from gelatinous or macroporous resins having a matrix with polystyrene (PS), or having a matrix with polyamide (PL) or polyethylene glycol (PEG), or else composite supports of polyethylene glycol-polystyrene (PEG-PS) or polyethylene glycol-dimethylacrylamide (PEGA).

A polymeric bead used as a starting material in the present invention preferably is a spherical copolymer bead having a particle diameter no greater than 200 microns (µm), preferably no greater than 170 µm, more preferably no greater than 150 µm, more preferably no greater than 125 µm, and most preferably no greater than 100 µm. Preferably, the bead has no void spaces having a diameter greater than 3 µm, more preferably no void spaces having a diameter greater than 2 µm, and most preferably no void spaces having a diameter greater than 1 µm. Typically, void spaces are readily apparent upon surface examination of the bead by a technique such as light microscopy.

Despite numerous advantages of solid supported chemistry for library generation, one of the crucial barriers during the synthetic steps is the stability of the functional group linking the first building block to the solid support. As a protecting group, the linker plays a key role in the choice of the synthetic strategy, determines conditions of the chemistry performed as well as conditions for anchoring and for releasing products from the solid support.

Moreover, the solid phase amino-alcohol of formula (I) which contains between 0,0001 and 10 mmol of amino alcohol moiety of formula (II):

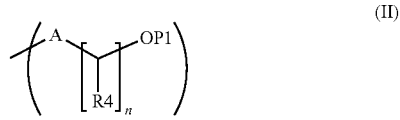

(II)

wherein A, R4, P1, and n are as defined above, per gram of solid support.

Preferably the substitution level of the amino alcohol moiety of formula (II) is comprised between 0,005 and 5 mmol per gram of solid support.

More preferably the substitution level of the amino alcohol moiety of formula (II) is comprised between 0,01 and 2,5 mmol per gram of solid support.

Therefore, in the present invention, a convenient linker is required to attach the nitrogen N of formula (I) to the solid support.

These considerations prompted the Inventors to use a versatile linker suitable for immobilization of electron-rich moieties including amines that could be applied to solid phase organic chemistry as well as to peptide and pseudopeptide chemistry by side-chain or in an N-terminus anchoring strategy.

Advantageously, the solid support is chosen in the group comprising acid-labile resins. Among linkers, TFA-labile ones are especially useful for the production of combinatorial libraries. Indeed, by using methodology cleavage and post-cleavage, workups are straightforward and often require only simple evaporation of TFA that can be done in parallel using vacuum centrifugator or inert gas bubbling.

According to these requirements, the trityl type of resins constitutes a good alternative and is preferred in the present invention.

Hindered trityl related linkers, such as 2-chloro chlorotrityl or 4-carboxy chlorotrityl linkers, provide a direct route to the anchoring of a wide variety of nucleophiles, and are therefore favored.

Aldehyde functionalized resins, p-nitrophenyl carbonate resin, preferably Wang or Merrifield resins, halomethyl resins and Rink acid trifluoracetate/chloride resins also constitutes good alternatives in the present invention.

Examples of aldehyde functionalized resins which can be used in the present invention comprise:

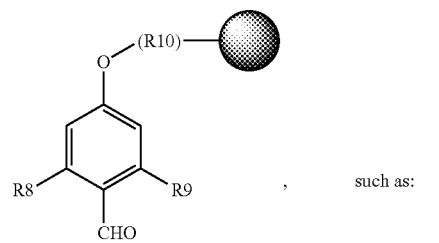

R8, R9 = H or OCH3
R10 = (C$_{1-6}$ alkyl)—CONH—

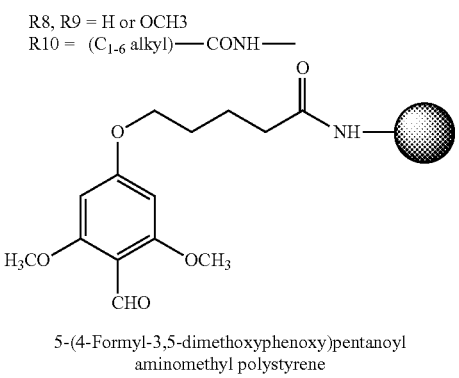

5-(4-Formyl-3,5-dimethoxyphenoxy)pentanoyl aminomethyl polystyrene

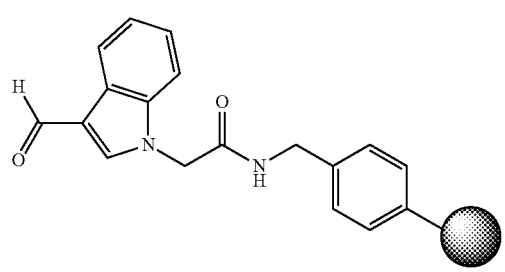

(3-Formylindolyl)acetamidom ethyl polystyrene

Examples of carbonate resins which can be used in the present invention comprise:

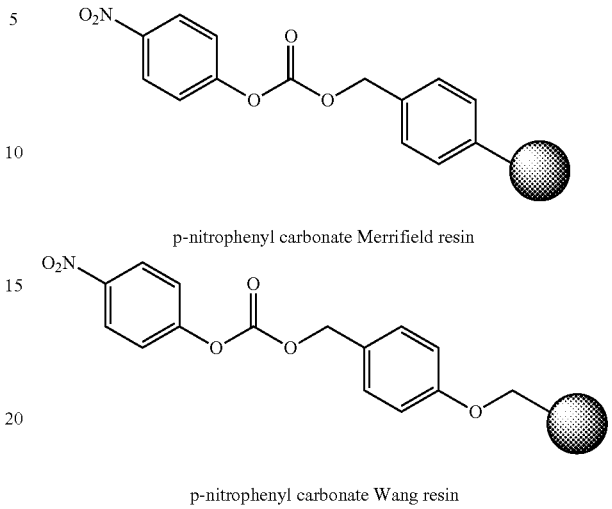

p-nitrophenyl carbonate Merrifield resin p-nitrophenyl carbonate Wang resin

Examples of halomethyl resins which can be used in the present invention comprise:

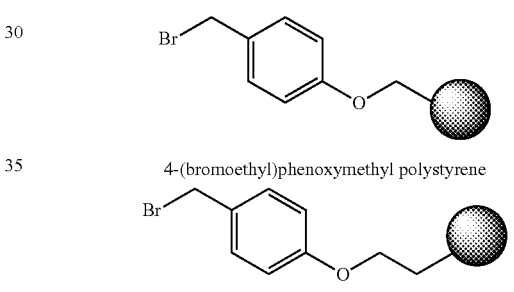

4-(bromoethyl)phenoxymethyl polystyrene 4-(bromoethyl)phenoxyethyl polystyrene

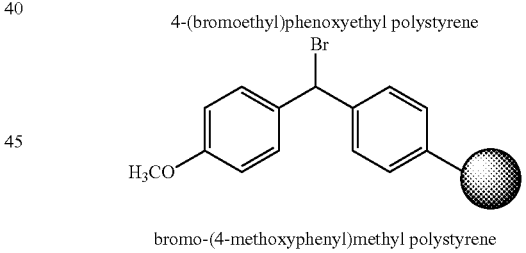

bromo-(4-methoxyphenyl)methyl polystyrene

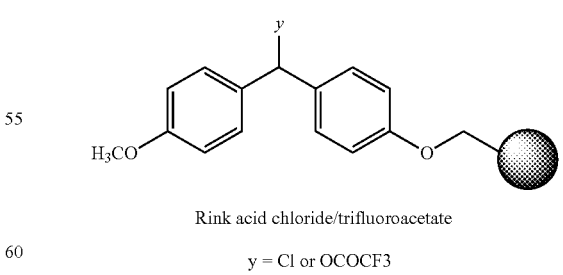

Rink acid chloride/trifluoroacetate y = Cl or OCOCF3 wherein, ● represents the base matrix, such as polystyrene.

General procedures for production and loading of resins using conventional techniques can be used in addition to, or in combination with, the techniques described herein.

Another object of the present invention relates to a solid phase depsipeptide having the following formula (III):

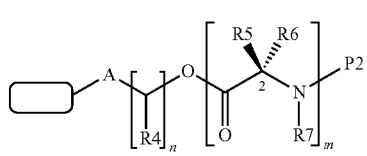

(III)

wherein:

☐, A, R4, n, are as defined above,

Each R5 and each R6 independently represent a hydrogen atom, a fluorine atom, a $C_1$-$C_{20}$ alkyl group, a $C_2$-$C_{10}$ alkenyl group, a $C_2$-$C_{10}$ alkynyl group, a ($C_4$-$C_{12}$) monocyclic or polycyclic hydrocarbonated group, a —($C_1$-$C_{10}$ alkyl)-($C_4$-$C_{12}$) monocyclic or polycyclic hydro carbonated group, a —($C_1$-$C_{10}$ alkyl)-S—($C_1$-$C_{10}$ alkyl) group, a —($C_1$-$C_{10}$ alkyl)-indol-2-yl group, —a ($C_1$-$C_{10}$ alkyl)-imidazolyl group, said groups being non substituted or substituted by 1 to 10 fluorine atoms, 1 to 5-NRR', 1 to 5SH, 1 to 5OR, 1 to 5COR, 1 to 5COOR, 1 to 5CONRR', 1 to 5NHCONH$_2$, and/or 1 to 5NHC(NH)NH$_2$ moieties wherein R and R' independently represent from one another a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, a —($C_1$-$C_{10}$ alkyl)-($C_4$-$C_{12}$) monocyclic or polycyclic unsaturated hydrocarbonated group, wherein the NH$_2$, NH, COOH, SH and OH functions of these groups are advantageously protected by one or several identical or different O-protecting and/or N-protecting and/or S-protecting groups or atoms.

Depsipeptides are as explained, modified peptides, i.e. isopeptides.

Advantageously, each R5, R6 and/or R7 independently are side chains of natural or unnatural amino acids.

More advantageously, R5, R6 and/or R7 independently are side chains of natural amino acids.

Even more advantageously, each R5 and/or R6 independently are side chains of natural or unnatural amino acids.

Most advantageously, R5 and/or R6 independently are side chains of natural amino acids.

In the case of proline, R7 and R5 or R7 and R6 form together with the atoms which carry them a 5-membered azacycloalkane ring.

When R5 and/or R6 are side chains of natural amino acids, the R5 and/or R6 residues may or may not be protected with standard protecting groups such as t-butyl (t-Bu), trityl (trt), benzyl (Bn or Bzl) and t-butyloxycarbonyl (Boc).

For example, in an Fmoc synthesis strategy, the t-Bu group is the preferred side-chain protecting group for amino acid residues tyrosine (Tyr), threonine (Thr), serine (Ser), glutamic acid (Glu) and aspartic acid (Asp); the Trt group is the preferred side-chain protecting group for amino acid residues histidine (His), glutamine (Gln) and asparagine (Asn); and the Boc group is the preferred side-chain protecting group for amino acid residues lysine (Lys) and tryptophane (Trp).

In a Boc synthesis strategy, side chains of natural amino acids may be protected with standard protecting groups such as benzyls ethers or esters or NO$_2$ for the arginine side chain, for example. These strategies and the carrying out of these strategies are well known by the skilled person in the art, and can be found in peptide synthesis dedicated books such as: Paul Lloyd-Williams, Fernando Albericio, Ernest Giralt, Chemical Approaches to the Synthesis of Peptides and Proteins, CRC Press, 1997 or Houben-Weyl Methods of Organic Chemistry, Synthesis of Peptides and Peptidomimetics, Vol E 22a, Vol E 22b, Vol E 22c, Vol E 22d., M. Goodmann Ed., Georg Thieme Verlag, 2002.

Advantageously, each R5 and R6 independently represent a hydrogen atom, a fluorine atom, a $C_1$-$C_{20}$ alkyl group, a $C_2$-$C_{10}$ alkenyl group, a $C_2$-$C_{10}$ alkynyl group, a ($C_4$-$C_{12}$) monocyclic or polycyclic hydrocarbonated group, a —($C_1$-$C_{10}$ alkyl)-($C_4$-$C_{12}$) monocyclic or polycyclic hydrocarbonated group, a —($C_1$-$C_{10}$ alkyl)-S—($C_1$-$C_{10}$ alkyl) group, a —($C_1$-$C_{10}$ alkyl)-indol-2-yl group, —a ($C_1$-$C_{10}$ alkyl)-imidazolyl group, said groups being non substituted or substituted by 1 to 10 fluorine atoms, 1 to 5-NRR', 1 to 5SH, 1 to 5OR, 1 to 5COR, 1 to 5COOR, 1 to 5CONRR', 1 to 5NHCONH$_2$, and/or 1 to 5NHC(NH)NH$_2$ moieties wherein R and R' independently represent from one another a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, a —($C_1$-$C_{10}$ alkyl)-($C_4$-$C_{12}$) monocyclic or polycyclic unsaturated hydrocarbonated group, wherein the NH$_2$, NH, COOH, SH and OH functions of these groups are advantageously protected by one or several identical or different O-protecting and/or N-protecting and/or S-protecting groups or atoms.

More advantageously, each R5 and each R6 independently represent a hydrogen atom, a $C_1$-$C_{20}$ alkyl group, a $C_2$-$C_{10}$ alkenyl group, a —($C_1$-$C_{10}$ alkyl)-aryl group, a —$C_1$-$C_{10}$ alkyl-OH group, a —$C_1$-$C_{10}$ alkyl-SH group, a —($C_1$-$C_{10}$ alkyl)-S—($C_1$-$C_{10}$ alkyl) group, a —($C_1$-$C_{10}$ alkyl)-indol-2-yl group, a —($C_1$-$C_{10}$ alkyl)-phenol group, a —($C_1$-$C_{10}$ alkyl)-CONH$_2$ group, a —($C_1$-$C_{10}$ alkyl)-imidazolyl group, a —($C_1$-$C_{10}$ alkyl)-COOH group, a —$C_1$-$C_{10}$ alkyl-NH$_2$ group, a —($C_1$-$C_{10}$ alkyl)-NHC(NH)NH$_2$ group, the NH$_2$, NH, COOH, SH and OH functions of these groups being advantageously protected by one or several identical or different O-protecting and/or N-protecting and/or S-protecting groups or atoms.

Even more advantageously, each R5 and each R6 independently represent a hydrogen atom, a —CH$_3$ group, a —CH(CH$_3$)$_2$ group, a —CH(CH$_3$)—CH$_2$CH$_3$ group, a —CH$_2$CH(CH$_3$)$_2$ group, a benzyl group, a —CH$_2$—OH group, a —CH(OH)—CH$_3$ group, a —CH$_2$—SH group, a —(CH$_2$)$_2$—S—CH$_3$ group, a —CH$_2$-indol-2-yl group, a —CH$_2$-phenol group, a —CH$_2$—CONH$_2$ group, a —(CH$_2$)$_2$—CONH$_2$ group, a —CH$_2$-imidazolyl group, a —CH$_2$—COOH group, a —(CH$_2$)$_2$—COOH group, a —(CH$_2$)$_4$—NH$_2$ group, a —(CH$_2$)$_3$—NHC(NH)NH$_2$ group, the NH$_2$, NH, COOH, SH and OH functions of these groups being advantageously protected by one or several identical or different O-protecting and/or N-protecting and/or S-protecting groups or atoms.

Each R7 independently represents a hydrogen atom, a $C_1$-$C_6$ alkyl group, a $C_2$-$C_6$ alkenyl group, a $C_2$-$C_6$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, a —($C_1$-$C_{10}$ alkyl)-($C_4$-$C_{12}$) monocyclic or polycyclic unsaturated hydrocarbonated group, or a CO—R group, wherein R represents a hydrogen, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, or a —($C_1$-$C_{10}$ alkyl)-($C_4$-$C_{12}$) monocyclic or polycyclic unsaturated hydrocarbonated group.

Advantageously, each R7 independently represents a hydrogen atom, a $C_1$-$C_6$ alkyl group, a $C_2$-$C_6$ alkenyl group, or a —($C_1$-$C_6$ alkyl)-aryl group. More advantageously, each R7 independently represents a hydrogen atom or a $C_1$-$C_6$ alkyl group.

R7 and R5, and/or R7 and R6 can form together with the atoms which carry them a monocyclic or polycyclic moiety wherein each ring is a 3- to 10-membered hydrocarbonated ring, saturated or unsaturated, the number of rings being comprised between 1 and 5, non substituted or substituted by 1 to 10 fluorine atoms, 1 to 5-NRR', 1 to 5SH, 1 to 5OR, 1 to 5COR, 1 to 5COOR, 1 to 5CONRR', 1 to 5NHCONH$_2$ and/or 1 to 5NHC(NH)NH$_2$ moieties wherein R and R' independently represent from one another a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, or a —($C_1$-$C_{10}$ alkyl)-($C_4$-$C_{12}$) monocyclic or polycyclic unsaturated hydrocarbonated group, wherein the NH$_2$, NH, COOH, SH and OH functions of these groups are advantageously protected by one or several identical or different O-protecting and/or N-protecting and/or S-protecting groups or atoms.

Advantageously, R5 and R7 and/or R6 and R7 can form together with the atoms which carry them a 4- to 10-membered azacycloalkane ring.

Even more advantageously, R5 and R7 and/or R6 and R7 can form together with the atoms which carry them a 5-membered azacycloalkane ring.

m is an integer from 1 to 100.

Advantageously, m is an integer between 1 and 50.

More advantageously, m is an integer between 1 and 25.

P2 represents a hydrogen atom or an N-protecting group.

P2 is preferably a Fmoc protecting group or a Boc protecting group.

P2 is even more preferably a Fmoc protecting group.

In formula (III), the carbon to which are linked R5 and R6 is referred to as "$C_2$".

Each $C_2$ can have independently an R or S configuration if said $C_2$ is an asymmetrical carbon.

Another object of the present invention relates to a process for producing a solid phase amino alcohol of formula (I), wherein it comprises the reaction of the amino alcohol of the following formula (IV):

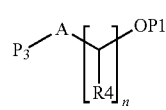

(IV)

wherein, A, R4, n, P1 are as defined above,

P3 represents a hydrogen atom or a leaving-N-protecting group,

P3 is preferably a hydrogen atom, with an activated solid support of the following formula (V):

(V)

wherein:

□ is a solid support as defined above,

X represents an activating group comprising chlorides, bromides, iodides, p-nitrophenolate.

The processes known to produce the amino alcohol of formula (IV) are well known in the art. For example, it is convenient, as it was done in the present case, to start from a commercially protected amino acid. It is then possible to reduce a mixed anhydride of this commercial protected amino acid by using a hydride generating compound such as NaBH$_4$, in the adequate solvents of course.

The process for producing a solid phase amino alcohol of formula (I) wherein it comprises the reaction of the solid phase amino alcohol of the following formula (IV) and an activated solid support of formula (V) is done in the presence of a base in an organic solvent.

The term "leaving-N-protecting group" means that initially the compound of formula (IV) has a P3 which is different to H, but an in situ reaction of deprotection, i.e. replacement of the P3 N-protecting group by a hydrogen atom, is carried out. For example, P3 is a Fmoc group, and a non nucleophilic base, such as 1,8-diazabicyclo[5.4.0]undec-7-ene (DBU) enabling to take the Fmoc group off, is added.

The term "activated solid support" means a solid support which comprises an activating group on the linker of said solid support.

The term "activating group" means a good leaving group which can comprise halides, or other groups as mentioned above.

The activation can also be done onto a hydroxy group instead of "X", by the use of an adequate coupling agent. "X" becomes then the activated moiety produced by the coupling agent.

All these activating methods are well known by the skilled person in the art.

Another object of the present invention relates to a process for producing a solid phase depsipeptide (III) in which m=1, wherein it comprises the following steps:
(a) removal of the O-protecting group P1, off the solid phase amino alcohol (I) as defined above, when P1 is not a hydrogen atom,
(b) coupling a conveniently protected amino acid of formula (VI):

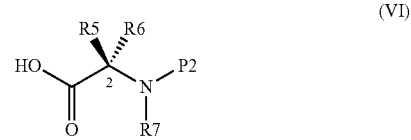

(VI)

wherein
R5, R6, R7, P2 and the fragment —COC(R5R6)NR7- are as defined above, with the solid phase amino alcohol obtained in step (a) by the use of at least one coupling agent in an organic solvent.

Removal of the O-protecting group P1 of step (a) is carried out in conditions well known from the skilled person in the art. The protecting group can be removed to regenerate the original hydroxy group. These conditions can be found for example in Greene, "Protective Groups in Organic Synthesis", Wiley, New York, 2007 4th edition; Harrison et al. "Compendium of Synthetic Organic Methods", Vol. 1 to 8 (J. Wiley & sons, 1971 to 1996); Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol E 22a, Vol E 22b, Vol E 22c, Vol E 22d., M. Goodmann Ed., Georg Thieme Verlag, 2002.

The coupling reaction of step (b) may be carried out by employing a condensing reagent such as N,N'-dicyclo hexylcarbodiimide (DCC) or 1-ethyl-3-(3'-dimethylaminopropyl) carbo diimide hydrochloride (EDC), i.e. water-soluble carbodiimide, O-(1H-benzotriazol-1-yl)-N,N,N',N'-tetramethyluronium tetrafluoroborate (TBTU), benzotriazol-1-yl-oxytris(dimethylamino)phosphonium hexafluorophosphate (BOP), O-(7-azabenzotriazol-1-yl)-1,2,3-tetramethyluronium hexafluorophosphate (HATU), O-benzotriazol-1-yl-N,N,N',N'-tetramethyluronium hexafluorophosphate (HBTU), O-benzotriazol-1-yl-tetramethyltetrafluoroborate (TBTU), N-hydroxy-5-norbornene-2,3-dicarbodiimide, or any other coupling agent in a solvent such as ether, acetone, chloroform, dichloromethane, ethyl acetate, DMF, tetrahydrofuran (THF), acetonitrile, dimethylsulfoxide (DMSO), N-methyl pyrrolidinone (NMP), under ice-cooling or at room temperature, preferably in the presence of an acylation catalyst such as dimethylaminopyridine (DMAP), pyridine, N-hydroxybenzotriazole (HOBt), 1-hydroxy-7-azabenzotriazole (HOAt), N-hydroxysuccinimide and the like.

Preferably the coupling reaction is carried out by employing DCC, DMAP in an organic solvent such as DCM and/or DMF.

In formula (VI), P2 is preferably a Boc group or a Fmoc group.

In formula (VI) and in the case of P2 being a Fmoc group, depending on which amino acid is being loaded, its side chain may or may not be protected. For example, when Tip is loaded, its side chain should be protected with Boc. Similarly, the side-chain of Gln may be protected with Trt, and so-on.

A Mitsunobu reaction can be used in the present invention to diminish racemisation of the amino acid whilst coupling it to the compound of formula (I). This system of esterification is described to lead to low levels of substitution but to preserve chiral integrity. However, the experimental results (see examples, step 3) in the present invention showed that the Mistunobu reaction can quite easily be compared to more typical techniques used in peptide synthesis.

It was noticed that the Mitsunobu reaction was particularly useful in the case of coupling a cysteine residue.

Therefore, the Mitsunobu reaction can be used for any other amino acid, natural amino acids or unnatural amino acids, as defined above.

Advantageously, the process for producing a solid phase depsipeptide (III) in which m=1 is achieved in step (b) of coupling by a Mitsunobu reaction.

Advantageously, the process for producing a solid phase depsipeptide (III) in which m=1 and the amino acid (VI) is Cys, is achieved in step (b) of coupling by a Mitsunobu reaction.

The classic Mitsunobu reaction (Mitsunobu 1981) employs a trivalent phosphorous reagent ($R_3P$) and an azo-containing reagent (—N=N—) to activate a functional group (e.g. hydroxyl) of reactant (R—OH). Reaction with a nucleophile reactant (Nu-H, e.g. $RCO_5H$, RCOSH, $R_2NH$, ArOH, TsOH, $R_3SiOH$, Halide) then forms the Mitsunobu product (R-Nu).

Preferably the Mitsunobu reaction is carried out by employing the protected amino acid, diethyl-azodicarboxylate (DEAD), triphenylphosphine in THF. The experimental conditions of the Mitsunobu reaction are well known by the skilled person in the art.

Another object of the present invention relates to a synthesis kit for the process for producing a solid phase depsipeptide (III), comprising:
a. a solid phase amino alcohol having the following formula (I):

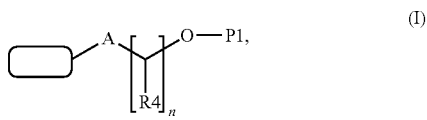

wherein ▭, A, R4, n, P1 are as defined above.
b. a trivalent phosphorous reagent as defined above, and
c. an azo containing reagent as defined above.

By trivalent phosphorous it is meant usual trivalent phosphorous reagent ($R_3P$) used in the Mitsunobu reaction, such as trialkylphosphine, triarylphosphine, diarylalkylphosphine, dialkylarylphosphine, and the like, preferably triphénylphosphine. By azo containing reagent it is meant usual azo containing reagent (—N=N—) used in the Mitsunobu reaction, such as diethyl-azodicarboxylate DEAD, dimethyl-azodicarboxylate DMAD, diisopropyl-azodicarboxylate, and the like, preferably diethyl-azo dicarboxylate DEAD.

The synthesis kit can comprise a supplementary element:
d. an amino acid.

By amino acid it is meant natural amino acids or unatural amino acids as defined above. Preferably the amino acids are chosen from easily epimerisable/racemisable amino-acids, such as Cystein or Histidine.

In a particular embodiment of the invention, the kit has its compounds b, c and/or d, pre-dissolved in one or several solvents.

The synthesis kit can comprise yet a supplementary element: e. one ore several additional solvents.

The latter can be identical or different to the solvents in which the compounds b, c and/or d, are pre-dissolved.

The solvents are independently usual organic solvents, especially ones used in the Mitsunobu reaction, such as aliphatic ether, cyclic ethers, such as THF. Preferably the solvents are anhydrous, or contain at least less than 5% in mass of water.

The concentrations of the pre-dissolved b, c and/or d compounds are adapted in view to be used in a Mitsunobu reaction. For example, the concentrations can range from 5% to 80% in mass of compound per volume of solvent, preferably 40% in mass of compound per volume of solvent.

Preferably the compounds, which can be either pre-dissolved or not, are in air tight sealed containers, such as vials or flasks, in a way that the skilled person in the art can directly use the compounds in the synthesis of the depsipeptides (III).

Another object of the present invention relates to the C to N peptide synthesis process for producing a solid phase depsipeptide (III) in which m is greater than 1 comprising the following successive steps:

(c) removal of the terminal-N-protecting group P2 off the depsipeptide (III) for which m=1, (d) coupling the solid phase depsipeptide obtained in step (c), with an N-protected amino acid (VI) as defined above, which side chain can carry an appropriate protecting group, thereby creating a new solid phase protected depsipeptide, (e) optional removal of the terminal-N-protecting group P2 off the depsipeptide obtained in step (d), (f) optionally repeating steps (d) and (e) as many times as necessary in order to obtain the desired solid phase depsipeptide (III).

Removal of the protecting group in the steps for the preparation of the depsipeptide of the invention is required to leave the protecting group without giving any influence upon the peptide linkage, and may be appropriately selected in compliance with the type of the protecting group used.

The coupling reaction may follow any methods conventionally employed for peptide synthesis, for example, employing a condensing agent method, an azide method, a chloride method, an acid anhydride method, a mixed anhydride method, an active ester method, an enzyme method as disclosed in Nobuo Izumiya et al., "Fundamentals and Experiments for Peptide Synthesis (in Japanese)", issued from Maruzen Co., Ltd., 1985, or a standard Fmoc protocol, see e.g. Carpino et al., 1970, J. Am. Chem. Soc. 92(19):5748-5749; Carpino et al., 1972, J. Org. Chem. 37(22):3404-3409.

Surprisingly, when m=2 and after deprotection of the terminal amine, no diketopiperazine formation is observed.

The C to N peptide synthesis process can comprises before or after step (e), a further step ($e_1$) of deprotecting at least one of the side chains R4, R5, R6, R7 and/or in A.

This is particularly interesting in view to attach on at least one of the side chains of the depsipeptide, for example an amino acid or a bio-organic molecule such as biotin. This strategy can be generalised to other molecules, such as carbohydrates, cryptands such as crown ethers, etc.

This process can also be carried out after step (f), a further step ($f_1$) of deprotecting at least one of the side chains R4, R5, R6, R7 and/or in A.

This process can also be carried out after a cleavage step, wherein adequate protecting groups have been left on the depsipeptide (III) and a further step ($f_2$) of deprotecting at least one of the side chains is done.

In addition and in specific cases, peptide fragments of the present invention can be synthesised using a combination of solid phase and solution phase synthesis techniques.

Solution phase synthesis techniques can be used for, for example, introducing functions or groups in ways incompatible with solid phases. The insertion of such steps can be made at any convenient moment of the syntheses.

A column method or a batch method may be also applicable herein.

Any protecting procedure is preferably applied to the carboxyl group, amino group, w-carbamido group and the like which would not participate in the said condensation reaction, according to any conventional and well-known procedures, before carrying out the condensation reaction.

In this case, various protecting groups as mentioned above may be applied for the said protecting procedure.

Another object of the present invention relates to the process for producing the following depsipeptide of formula (VII):

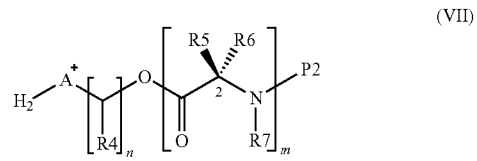

(VII)

wherein A, R4, R5, R6, R7, $C_2$, P2, n, m are as defined above, which consists in the carrying out of the processes disclosed above to obtain a depsipeptide (III), and to proceed to an acidic cleavage step (g) to remove the solid support ▭.

Peptides synthesized via solid phase synthesis techniques can be cleaved and isolated according to, for example, the following non-limiting techniques: the peptide may be cleaved from the resin using techniques well known to those skilled in the art. For example, solutions of 1% or 2% trifluoroacetic acid (TFA) in dichloromethane (DCM) or a combination of a 1% and a 2% solution of TFA in DCM may be used to cleave the peptide, or a 10% solution of trifluoroethanol (TFE) in DCM may also be used. Acetic acid (HOAC), hydrochloric acid (HCl) or formic acid may also be used to cleave the peptide. In theses cases the recovered peptide are fully protected except the NH in the C-terminal position. The specific cleavage reagent, solvents and time required for cleavage will depend on the particular peptide being cleaved.

Higher concentrations of acids or strongly acidic conditions such as HF in the case of for example carbonate Merrifield resin may be used to also remove the protecting groups on the depsipeptide. It is advantageous to use scavengers, such as silanes or other scavenger cocktails (especially for cation- and/or acid-sensitive side chain (or group) incorporating peptides), to prevent any side reactions. It is advantageous to cumulate the N-terminal-deprotecting step with the cleavage of the depsipeptide (III). For example, if no other coupling reaction is to be carried out on the nitrogen linked to R5, it is advantageous that P2 is a Boc group, so that during cleavage the use of TFA will also remove P2.

After cleavage the cleavage fractions are subjected to standard work-up procedures to isolate the peptide. Typically, the combined cleavage fractions are concentrated under vacuum, followed by reconstitution with polar aprotic or polar aprotic solvents such as ethanol (EtOH), methanol (Me-OH), isopropyl alcohol (IPA), acetone, acetonitrile (ACN), dimethyl formamide (DMF), DCM, etc., followed by precipitation or crystallization with antisolvent such as water, diethyl-ether or hexanes, and collection by vacuum filtration. Alternatively, the product may be triturated with organic solvents or water after isolation of the peptide.

Another object of the present invention relates to the process for the synthesis of the following peptide alcohol of formula (VIII):

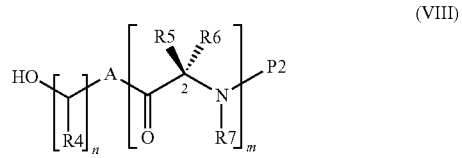

(VIII)

wherein A, R4, R5, R6, R7, $C_2$, P2, n, m are as defined above, wherein it comprises a step (h) of O—N acyl shift of the depsipeptide of formula (VII), using organic basic conditions or buffered conditions.

Basic conditions means by adding any base known by the skilled person in the art, either organic or mineral, in whatever form it can be, i.e. as a solution, a solid, or as a gas, diluted or dissolved in a mineral or organic solvent. Thus organic or inorganic bases may be used. Suitable organic bases for example include amines, either primary, secondary or tertiary. Tertiary amines are preferred. Examples of suitable amines include cyclo hexylamine, 1,5-diazabicyclo-[5,4,0]-undec-5ene, piperidine, ethanolamine, pyrrolidine, diethylamine, morpholine, piperazine, dicyclohexylamine, hydroxylamine, hydrazine, N,N'-isopropylethylamine, N,N,N',N'-tetramethyl-1,8-naphtalenediamine, tributylamine, triethylamine and triethylendiamine, and the like.

Inorganic bases for example include sodium hydroxide, potassium hydroxide, sodium and potassium carbonates, sodium and potassium phosphates, ammonia and the like. Advantageously, dimethylformamide and piperidine are used in step (h).

By buffered conditions it is meant by adding any buffer known to the skilled person in the art, either organic or mineral, in whatever form it can be, i.e. as a solution, a solid, or as a gas, diluted or dissolved in a mineral or organic solvent. Advantageously, the pH is comprised between 4 and 9. Even more advantageously, the pH is comprised between 7 and 8. Most advantageously, the pH is about 7.4. Said buffer can be chosen between sodium and potassium carbonates, sodium and potassium phosphates, and can be used with oxidation agents or resins such as Oxyfold resin.

Advantageously, an aqueous phosphate buffer with or without Oxyfold resin are used in step (h).

The Oxyfold resin enables to bond together the sulphur atoms of the two Cys amino acid residues, when needed.

In the present invention, a solid phase amino alcohol of formula (I) is used to synthesise a solid phase depsipeptide (III), and/or to synthesise the peptide alcohol as defined in formula (VIII).

In the present invention, a solid phase depsipeptide (III) is used to synthesise a peptide alcohol as defined in formula (VIII).

The invention is further embodied in the following non-limiting examples and figures. In these Examples, 7 peptides sequences were synthesised:

```
SEQ ID n°1: Gramicidin A derivative:
H-Trp-DLeu-Trp-DLeu-Trp-Gly-ol
SEQ ID n°2: Trichogin GA IV derivative:
H-Aib-Gly-Leu-Aib-Gly-Gly-Leu-Aib-Gly-Ile-Leu-ol
SEQ ID n°3: 1c:Octreotide:
H-DPhe-Cys-Phe-DTrp-Lys-Thr-Cys-Thr-ol
```
```
SEQ ID n°4: Isogalanin formula:
H-Gly-Trp-Thr-Leu-Asn-Ala-Ala-(D)Trp-Tyr-Leu-Leu-Gly-Pro-His-o-Ala-H
SEQ ID n°5: Galanin Formula:
H-Gly-Trp-Thr-Leu-Asn-Ala-Ala-(D)Trp-Tyr-Leu-Leu-Gly-Pro-His-Ala-ol
SEQ ID n°6: synthesis intermediate:
H-Gly-Trp-(Boc)-Thr(tBu)-Leu-AsN(Trt)-Ala-Ala-(D)Trp(Boc)-Tyr(tBu)-Leu-Leu-Gly-Pro-His(Trt)-o-Ala-Trt resin
SEQ ID n°7: synthesis intermediate:
H-Gly-Trp-Thr-Leu-Asn-Ala-Ala-(D)Trp-Tyr-Leu-Leu-Gly-Pro-His-o-Ala-H₂⁺
```

EXAMPLES

In the present invention, the following abbreviations are used: AA, amino acid; Aib (2-Amino isobutyric acid); BOP, O-(1H-benzotriazol-1-yl)-1,1,3,3-tetramethylphosphonium hexafluorophosphate; DCM, dichloromethane; DIC, diisopropylcarbodiimide; DCC, dicyclohexylcarbodiimide; EDC, 1-Ethyl-3-(3-dimethyllaminopropyl)carbodiimide; DIEA, diisopropylethylamine; DMF, dimethylformamide; PyBop, (Benzotriazol-1-yloxy)tripyrrolidinophosphonium hexafluorophosphate; PyBrop, Bromo-tris-pyrrolidino phosphoniumhexafluorophosphate; HBTU, O-Benzotriazole-N,N,N',N'-tetramethyl-uronium-hexafluoro-phosphate; HATU, N-[(dimethylamino)-1H-1,2,3-triazolo-[4,5-b]pyridine-1-yl-methylene]-N-methylmethanaminium hexafluorophosphate N-oxide; HOBt, hydroxybenzotriazole; HOAt, 1-Hydroxy-7-azabenzotriazole, HPLC, High Performance Liquid Chromatography; IBCF, isobutyl chloroformate, LC/MS, Tandem Liquid Chromatography/Mass Spectroscopy; PS, polystyrene; SPPS, Solid Phase Peptide Synthesis; TEA, triethylamine; NMM, N-methyl morpholine; TFA, trifluoroacetic acid; THF, tetrahydrofurane; TIS, triisopropylsilane; EDT, ethanedithiol. Other abbreviations used were those recommended by the IUPAC-IUB Commission (Eur. J. Biochem. 1984, 138, 9-37).

The activation reagents were purchased from Iris Biotech GmbH, Novabiochem, Senn Chemicals, other reagents from Iris Biotech GmbH, .Novabiochem, Senn Chemicals. Aminoacids derivatives were purchased from Iris Biotech GmbH, Novabiochem, Senn Chemicals, Neosystem.

N.B.: —In the hereunder examples, when not specified, TFA cleavages (i.e. use of commercial TFA) are advantageously done with scavengers such as TIS or EDT. The carrying out of these cleavages is well known in the art.
— The numbering of the molecule in the hereunder examples is specific to each example, i.e. molecule 1a of example 1 is different to molecule 1a of example 2.

The invention is further embodied in the following non-limiting examples and figures.

FIGURES

FIG. 1: Epimerization control of the Cysteine residue during acylation by method 1 or 2: HPLC chromatogram (chiralcel OD-RH. column; detection at 214 nm; elution under isocratic conditions: 70% of H₂O/0.1% TFA and 30% of CH₃CN/0.1% TFA during 30 min at a flow rate of 0.7 mL/min of the crude Fmoc(L and or /D)Cys-Throf (7c, 7c-(D), 7c')

Figure 2:
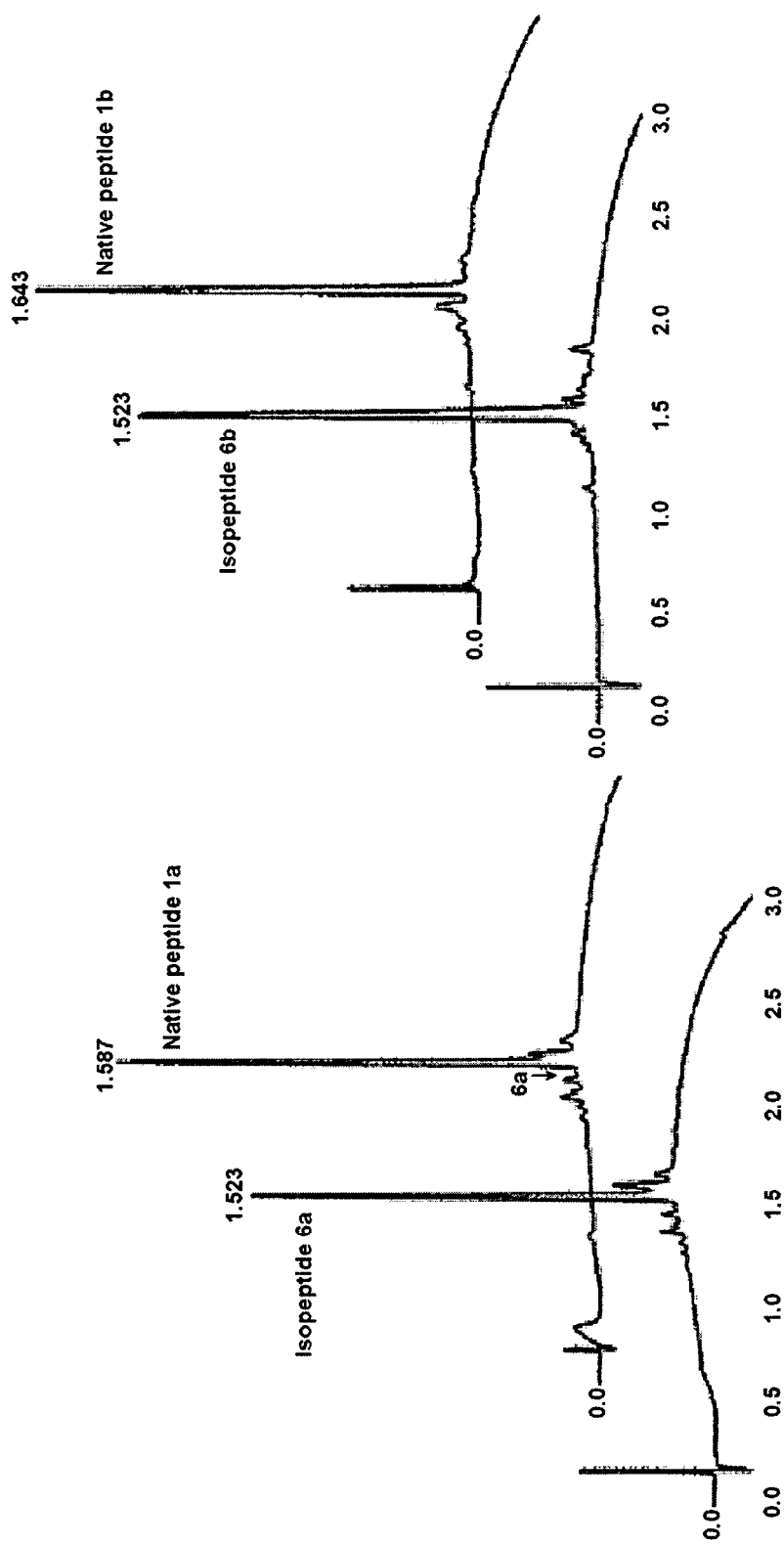

FIG. 2: O—N-acyl migration reaction

Figure 3:
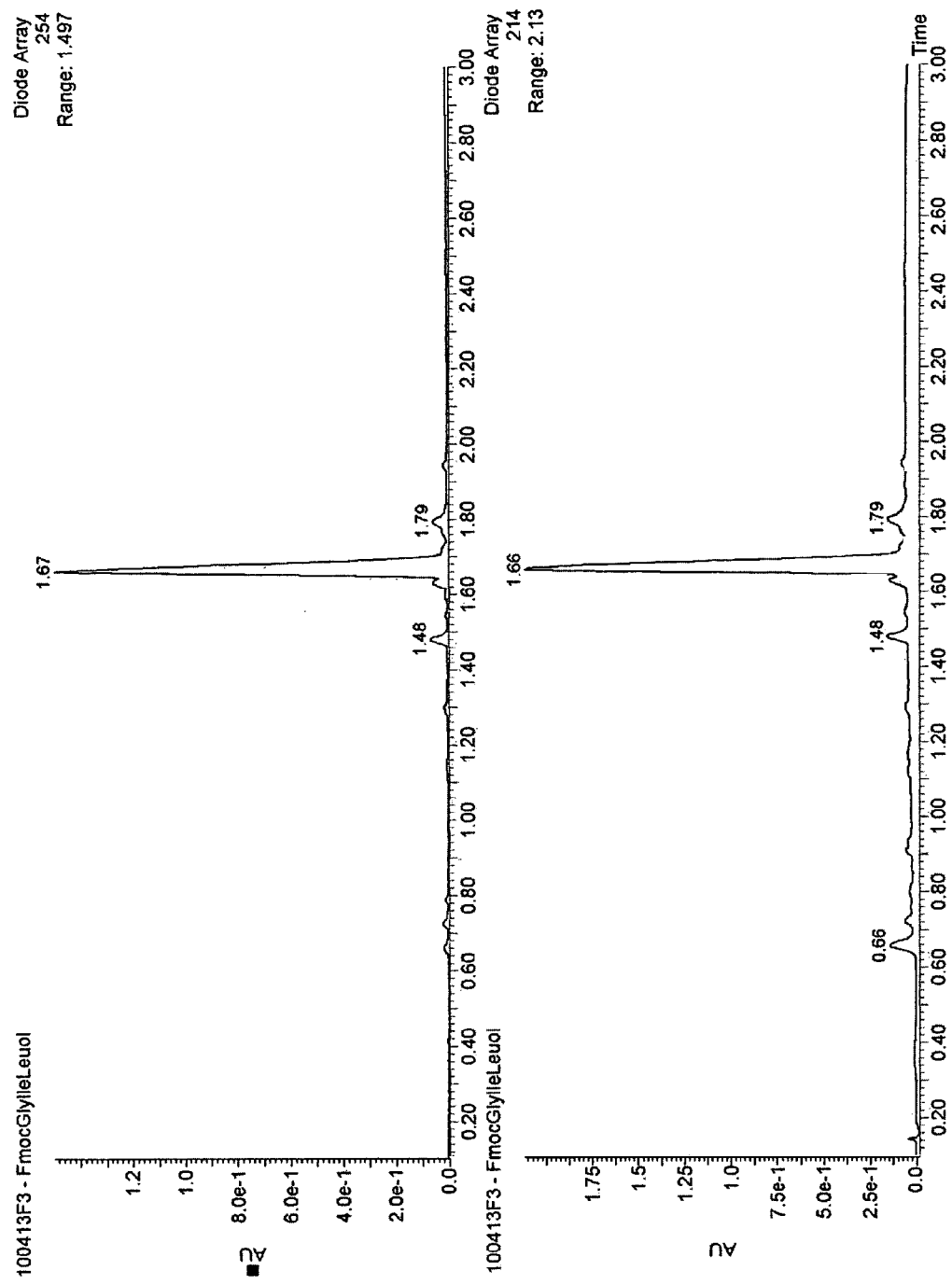

FIG. 3: HPLC diagrams at 254 and 214 nm of Fmoc-Gly-Ile-Leu-ol obtained by the process of the present invention (extracted from example 3, here-under). The transition isopeptide Fmoc-Gly-Ile-o-Leu-H has a retention time of 1.46 min (thus the peak at 1.48 minutes in FIG. 3 could be the residual isopeptide).

Example 1

Synthesis of a Gramicidin A derivative, Trichogin GA IV Derivative and Octreotide The following examples show each step in the synthesis of 3 different compounds using the products and processes of the present invention.

Three peptide alcohol models 1a-c were synthesized using this approach combining the synthesis of depsipeptides onto a solid support and the O—N acyl transfer reaction in solution.

(SEQ ID n°1)
1a: Gramicidin A derivative: H-Trp-DLeu-Trp-DLeu-Trp-Gly-ol (SEQ ID n°2)
1b: Trichogin GA IV derivative: H-Aib-Gly-Leu-Aib-Gly-Gly-Leu-Aib-Gly-Ile-Leu-ol (SEQ ID n°3)
1c: Octreotide: H-DPhe-Cys-Phe-DTrp-Lys-Thr-Cys-Thr-ol

Step 1: Synthesis of the Amino Alcohols from the Corresponding Amino Acid

N-Fmoc β-amino alcohols 2a-c were obtained by $NaBH_4$ reduction of mixed anhydrides of N-Fmoc amino acids in an organic/aqueous medium as previously described.

Synthesis scheme 1

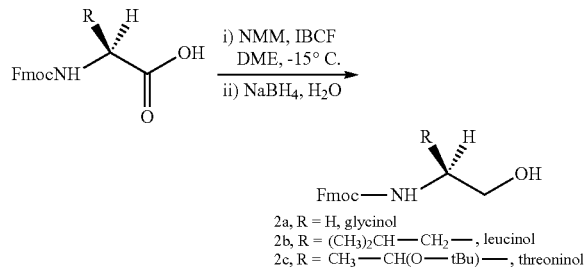

2a, R = H, glycinol
2b, R = $(CH_3)_2CH-CH_2-$, leucinol
2c, R = $CH_3-CH(O-tBu)-$, threoninol

Step 2: Synthesis of the Solid Phase Amino Alcohols (I)

N-Fmoc protected-amino alcohols 2a-c were directly engaged in a one-pot Fmoc-, deprotection and resin loading reaction using a 2% DBU solution in anhydrous DMF to afford the amino alcohol functionalized resins 3a-c.

Synthesis scheme 2

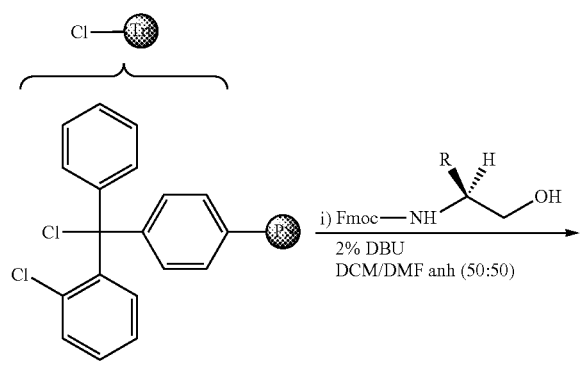

i) Fmoc-amino alcohols (3 eq), 2% DBU in anhydrous DCM/DMF (50/50), RT, 12 h.

Step 3: Synthesis of the Solid Phase Depsipeptide (III) with m=1

Then the free hydroxyl function was acylated with suitable protected-amino acid by DIC/DMAP to afford supported compounds 4a-b and 4c'.

When DIC/DMAP acylation was performed with Fmoc-Trp(Boc)-OH and Fmoc-Ile-OH, to produce peptide alcohols 1a and 1b, no epimerization was detected. However, acylation of cysteine residue, which is known to be sensitive to epimerization, occurred with a substantial level of epimerization (30%). This extent of epimerization was analyzed after TFA/TIS/$H_2O$/EDT treatment of a small sample 4c' on chiral RP-HPLC Synthesis scheme 3

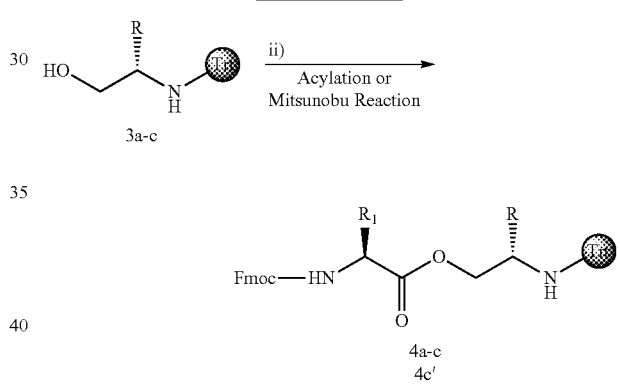

ii) Method 1 for 4a-b and 4c': Fmoc-AA-OH (6 eq), DIC (3 eq), DMAP (0.3 eq), anh. DCM/DMF (50/50), RT, 12 h or Method 2 for 4c: Mitsunobu conditions for Cys residue; Fmoc-(L and D)-Cys(Trt)-OH (3 eq), $PPh_3$ (3 eq), DEAD (3 eq) in THF anh. RT, 2×6 h.

In the search of a general epimerization-free anchoring system, the polymer supported amino alcohol 3c was esterified by Fmoc-(L and D)-Cys(Trt)-OH using the Mitsunobu reaction, which is not extensively used in SPPS (synthesis scheme 4), to afford compounds 4c and 4c-(D). This system of esterification is described to lead to low level of substitution but to preserve chiral integrity. In our case, as expected epimerization was not detected (compounds 7c and 7c-(D)). After treatment at room temperature 2×6 h the estimated loading was the same than that obtained with DCC/DMAP (0.47 mmol/g, 61% yield). Moreover, epimerization of cysteine linked to a resin via an ester bond during peptide-chain elongation using the Fmoc/tBu strategy was also analyzed by synthesizing the D-Cys containing octreotide. It is noteworthy that no racemization was observed (supporting information).

Synthesis scheme 4

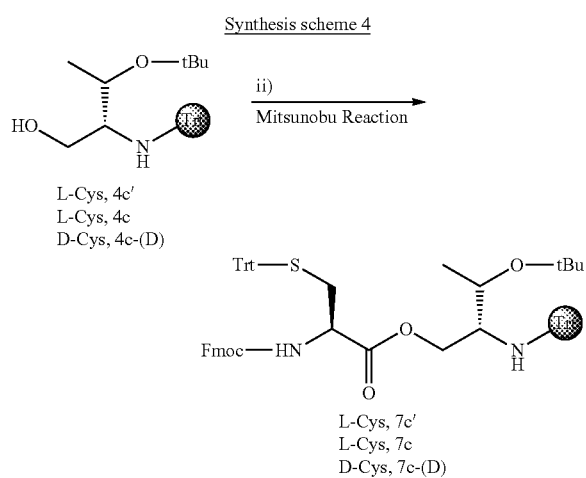

L-Cys, 4c'
L-Cys, 4c
D-Cys, 4c-(D)

L-Cys, 7c'
L-Cys, 7c
D-Cys, 7c-(D)

Step 4: Synthesis of the Solid Phase Depsipeptide (III) with m>1

Synthesis scheme 5

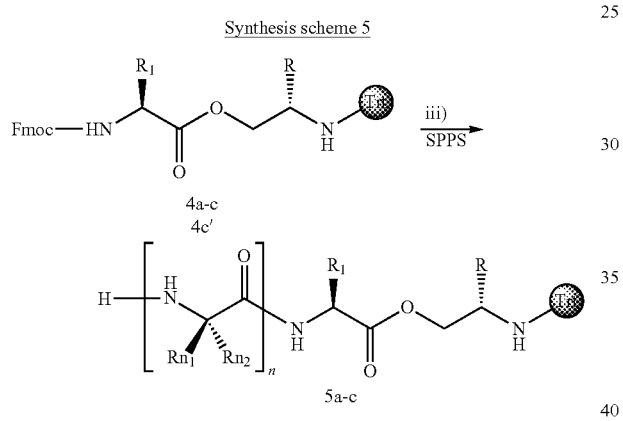

iii) SPPS: deprotection: Pip/DMF (20/80); coupling: Fmoc-AA-OH (3 eq), HBTU (3 eq)/DIEA (6 eq), DMF.

During the synthesis of gramicidine, which contains an unfavourable L/D combination the risk of diketopiperazine formation was analyzed (see FIGS. 1 and 2). After 1 h DMF/Piperidine treatment no release of diketopiperazine [D-Leu-LTrp] was observed. The remaining target sequences were synthesized using HBTU/DIEA coupling strategy at room temperature or under microwave irradiation to yield the resin anchored-depsipeptides 5a-c.

Step 5: Cleavage of the Solid Phase Depsipeptide (III)

Resins 5a-c were cleaved using TFA treatment affording the free depsipeptides 6a-c with high purity (80-95%).

Synthesis scheme 6

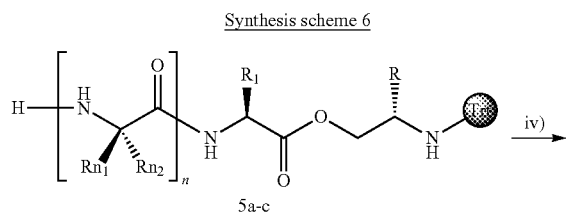

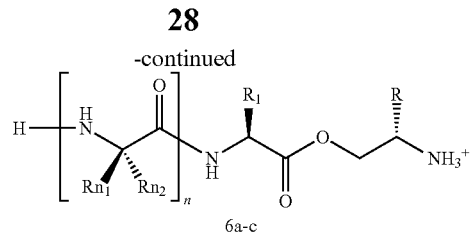

iv) cleavage: for 5a, TFA/TIS/H$_2$O (95/2.5/2.5), 1 h; for 5b TFA, 1 h; for 5c TFA/EDT/anisole/thioanisole (90/5/2.5/2.5), 2 h.

Step 6: O—N Intramolecular Acyl Migration

Compounds 6a-c were then submitted to the O—N-acyl migration reaction. They were dissolved and stirred in aqueous phosphate buffer at pH 7.4 or in organic conditions DMF/Pip (80/20) and the O—N intramolecular acyl migration for each compound was followed by RP-HPLC and LC/MS analyses.

Synthesis scheme 7

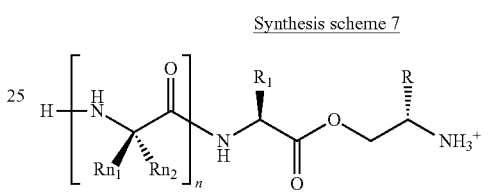

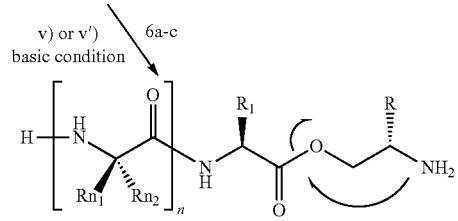

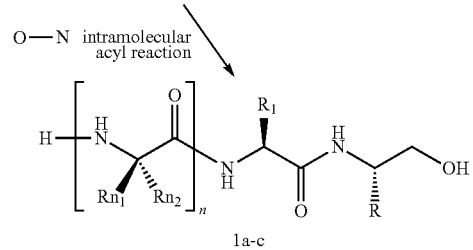

1a-c v) O—N acyl shift in the case of 6a and 6b: DMF/Pip (80/20) solution or v') O—N acyl shift and oxidation in the case of 6c: aqueous phosphate buffer pH 7.4 and Oxyfold resin (5 eq).

The intramolecular transposition reaction was quantitative in phosphate buffer or in organic conditions at room temperature after 1 h affording crude compounds Ia-b with good purity (80-95%) (see FIG. 2). The yields of recovered peptides were 80 to 90%, based on the initial resin loading. The yields of recovered peptides were 80 to 90%, based on the initial resin loading. For Octreotide 1c, migration and oxidation of 6c were performed one-pot by adding to the phosphate buffer, 5 equivalents of the Oxyfold resin for 6 h at room temperature.

Conclusion:

In this study, we have reported a general method for the synthesis of peptide alcohol starting from p-amino alcohols and using the O—N acyl transfer reaction. Several advantages can be pointed out: 1) rapid and efficient loading of the amino alcohol, 2) mild cleavage conditions associated with the possibility to recover a deprotected or a totally protected peptide alcohol, 3) no epimerization. Indeed, during acylation of the polymer-supported alcohol by cysteine derivative, the problem of large epimerization was totally suppressed by using the Mitsunobu reaction. Finally this methodology offers a method of choice for the preparation of this class of peptides.

Example 2

Generalization of the Peptide-Alcohol Synthesis Scaffolding

The compounds and methods disclosed in this example can be used in the syntheses of peptide alcohols according to the present invention. Many products were synthesised in this example, which proves the ease to carry out the present invention.

I. Synthesis of the Fmoc-β-Aminoalcohols

Synthesis scheme 8

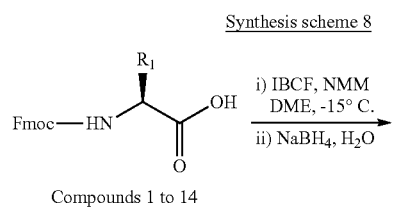

Compounds 1 to 14

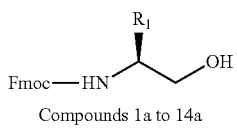

Compounds 1a to 14a

Synthesis of the Fmoc-β-Amino Alcohols

To a cold (−15° C.) solution of Fmoc-AA-OH (1 eq) in 1,2-dimethoxyethane (1 M) were successively added N-methyl morpholine (1 eq) and isobutyl chloroformate (1 eq). After a few minutes, a solution of sodium borohydride (1.2 eq) in water (1 M) was added at once (strong effervescence). The mixture was poured into a saturated aqueous $NaHCO_3$ solution. Then, the Fmoc-β-amino alcohol was extracted twice with ethyl acetate. The combined ethyl acetate phase was washed with a 1 M solution of $KHSO_4$, brine and dried over anhydrous $MgSO_4$. After removal of the solvent under reduced pressure, a solid residue was obtained.

Starting Materials:

TABLE 1

Starting materials: amino acids

| Cpd num | Compound | MW (g·mol⁻¹) | n (mmol) | Mass (g) |
|---|---|---|---|---|
| 1 | Fmoc-Ala-OH | 311.3 | 5.0 | 1.56 |
| 2 | Fmoc-Arg(Pbf)-OH | 648.8 | 5.0 | 3.24 |
| 3 | Fmoc-Asn(Trt)-OH | 596.7 | 5.0 | 2.98 |
| 4 | Fmoc-Asp(OtBu)-OH | 411.5 | 5.0 | 2.06 |
| 5 | Fmoc-Cys(Trt)-OH | 585.7 | 5.0 | 2.93 |
| 6 | Fmoc-Glu(OtBu)-OH | 425.5 | 5.0 | 2.13 |
| 7 | Fmoc-Gln(Trt)-OH | 610.7 | 5.0 | 3.05 |
| 8 | Fmoc-Ile-OH | 353.4 | 5.0 | 1.77 |
| 9 | Fmoc-Lys(Boc)-OH | 468.5 | 5.0 | 2.34 |
| 10 | Fmoc-Met-OH | 371.5 | 5.0 | 1.86 |
| 11 | Fmoc-Ser(tBu)-OH | 383.4 | 5.0 | 1.92 |
| 12 | Fmoc-Trp(Boc)-OH | 526.6 | 5.0 | 2.63 |
| 13 | Fmoc-Tyr(tBu)-OH | 459.5 | 5.0 | 2.30 |
| 14 | Fmoc-Val-OH | 339.4 | 5.0 | 1.70 |

"Cpd num" means "Compound number"

TABLE 2

Starting materials: other compounds

| Compound | MW (g·mol⁻¹) | n (mmol) | Qty |
|---|---|---|---|
| IBCF | 136.5 | 5.5 | 720 μl |
| NMM | 101.2 | 5.5 | 604 μl |
| DME | # | # | 50 ml |
| $NaBH_4$ | 38 | 6.3 | 0.24 g |
| $H_2O$ | # | # | qsfs |

"Qty": means "Quantity"
"qsfs": "Quantity sufficient for synthesis"

Results

TABLE 3

LC/MS Analysis of the obtained Fmoc-β-aminoalcohols and yields

| Cpd num | Compound | MW (g·mol⁻¹) | Mass (g) | Yield (%) | HPLC (214 nm) | [M + H]⁺ (Da) | [M + Na]⁺ (Da) |
|---|---|---|---|---|---|---|---|
| 1a | Fmoc-Ala-ol | 297.3 | 1.37 | 92 | 1.73 (100%) | 298.3 | 320.3 |
| 2a | Fmoc-Arg(Pbf)-ol | 624.4 | 2.99 | 94 | 2.12 (99%) | 625.4 | # |
| 3a | Fmoc-Asn(Trt)-ol | 582.5 | 2.89 | 99 | 2.32 (100%) | 583.5 | 605.6 |
| 4a | Fmoc-Asp(OtBu)-ol | 397.3 | 1.64 | 82 | 2.02 (100%) | 398.3 | 420.2 |
| 5a | Fmoc-Cys(Trt)-ol | 571.2 | 2.95 | 96 | 2.55 (100%) | 572.2 | 594.2 |
| 6a | Fmoc-Glu(OtBu)-ol | 411.3 | 1.87 | 90 | 2.05 (98%) | 412.3 | 434.3 |
| 7a | Fmoc-Gln(Trt)-ol | 596.2 | 2.98 | 99 | 2.32 (98%) | 597.3 | 619.3 |
| 8a | Fmoc-Ile-ol | 339.2 | 0.89 | 52 | 2.01 (100%) | 340.2 | 362.2 |
| 9a | Fmoc-Lys(Boc)-ol | 454.2 | 1.39 | 60 | 2.02 (100%) | 455.2 | 477.2 |
| 10a | Fmoc-Met-ol | 357.2 | 1.70 | 96 | 1.88 (98%) | 358.2 | # |
| 11a | Fmoc-Ser(tBu)-ol | 369.2 | 1.28 | 70 | 2.00 (100%) | 370.2 | 392.2 |
| 12a | Fmoc-Trp(Boc)-ol | 512.3 | 2.48 | 96 | 2.37 (100%) | 513.3 | 535.1 |
| 13a | Fmoc-Tyr(tBu)-ol | 445.2 | 2.13 | 94 | 2.18 (98%) | 446.2 | 468.2 |
| 14a | Fmoc-Val-ol | 325.2 | 0.85 | 52 | 1.92 (100%) | 326.2 | 348.2 |

"#": means that no peak was observed
"Cpd num" means "Compound number"

The NMR-$^1$H data are available, in particular in DMSO-d6, but not shown here.

II. Synthesis of the β-Aminoalcohols-Resins

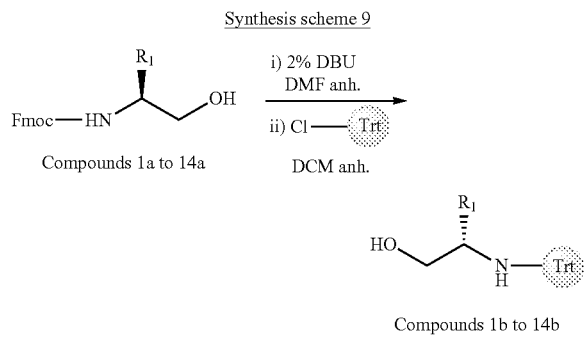

Compounds 1a to 14a → Compounds 1b to 14b

Synthesis scheme 9

Anchoring of the β-Amino Alcohols on the 2-Chlorotrityl Chloride Resin

The Fmoc-β-amino alcohol (3 eq) was dissolved in a 2% solution of DBU in anhydrous DMF and the resulting solution was added to the 2-chlorotrityl chloride resin (1.55 mmol g$^{-1}$). The reaction mixture was stirred at room temperature for 12 h, and the resin was then removed by filtration and washed with DMF (×3), 10% DIEA in MeOH (×3), DMF (×3), and CH$_2$Cl$_2$ (×3).

Starting Materials

Two batches of different grafted resins were synthesised: the first batch on 1 g of resin and the second batch on 500 mg of resin.

TABLE 4

Quantities of Fmoc-β-aminoalcohols separately used on batches of 1 g resin

| Cpd num | Compound | MW (g · mol$^{-1}$) | n (mmol) | Mass (g) |
|---|---|---|---|---|
| 1a | Fmoc-Ala-ol | 297.3 | 4.5 | 1.34 |
| 10a | Fmoc-Met-ol | 357.5 | 4.5 | 1.61 |
| 12a | Fmoc-Trp(Boc)-ol | 512.6 | 4.5 | 2.31 |
| 15a | Glycinol | 61.1 | 4.5 | 272 μl |
| 16a | Fmoc-Phe-ol | 373.4 | 4.5 | 1.68 |

"Cpd num" means "Compound number"

TABLE 5 other compounds used for the first batch synthesis of β-aminoalcohols-resins:

| Compound | Substitution | Qty |
|---|---|---|
| 2% DBU (V/V) | # | 160 μl |
| DMF anhydrous | # | 8 ml |
| Cl—⬤ | 1.55 (mmol · g$^{-1}$) | 1.0 g |
| DCM anhydrous | # | 8 ml |

"Qty": means "Quantity"

TABLE 6

Quantities of Fmoc-β-aminoalcohols separately used on batches of 0.5 g resin

| Cpd num | Compound | MW (g · mol$^{-1}$) | n (mmol) | Mass (g) |
|---|---|---|---|---|
| 2a | Fmoc-Arg(Pbf)-ol | 634.8 | 2.3 | 1.46 |
| 3a | Fmoc-Asn(Trt)-ol | 582.7 | 2.3 | 1.34 |
| 4a | Fmoc-Asp(OtBu)-ol | 397.5 | 2.3 | 0.91 |
| 5a | Fmoc-Cys(Trt)-ol | 571.7 | 2.3 | 1.31 |
| 6a | Fmoc-Glu(OtBu)-ol | 411.5 | 2.3 | 0.95 |
| 7a | Fmoc-Gln(Trt)-ol | 596.7 | 2.3 | 1.37 |
| 8a | Fmoc-Ile-ol | 339.4 | 2.3 | 0.78 |
| 9a | Fmoc-Lys(Boc)-ol | 454.5 | 2.3 | 1.05 |
| 11a | Fmoc-Ser(tBu)-ol | 369.4 | 2.3 | 0.85 |
| 13a | Fmoc-Tyr(tBu)-ol | 445.5 | 2.3 | 1.02 |
| 14a | Fmoc-Val-ol | 325.4 | 2.3 | 0.75 |

"Cpd num" means "Compound number"

TABLE 7 other compounds used for the second batch synthesis of β-aminoalcohols-resins:

| Compound | Substitution | Qty |
|---|---|---|
| 2% DBU (V/V) | # | 100 μl |
| DMF anhydrous | # | 5 ml |
| Cl—⬤ | 1.55 (mmol · g$^{-1}$) | 500 mg |
| DCM anhydrous | # | 5 ml |

"Qty": means "Quantity"

III. Cleavage of the β-Aminoalcohols-Resins

A way to check if the β-aminoalcohols are grafted onto the resin is to treat said resin with cleaving agents, such as the mixture TFE/AcOH/DCM, and analyse the product rinsed off.

Synthesis scheme 10

Compounds 1b to 14b →(TFE/AcOH/DCM, v/v/v, 20/10/70)→ Compounds 1c to 14c

The resin was cleaved from the resin by using a solution of TFE/AcOH/DCM (v/v/v, 20/10/70) for 1 h at room temperature. After filtration, the solution was concentrated under reduced pressure and analyzed by mass spectrometry. Other cleavage techniques commonly used in the organic synthesis field could also have been used.

TABLE 8

Cleavage of the β-aminoalcohols-resins:

| Cpd num | Compound | MW (g · mol$^{-1}$) | [M + H]$^+$ (Da) |
|---|---|---|---|
| 1c | H-Ala-ol | 85.1 | 86.0 |
| 2c | H-Arg(Pbf)-ol | 412.3 | 413.2 |
| 3c | H-Asn(Trt)-ol | 360.2 | 361.2 |
| 4c | H-Asp(OtBu)-ol | 175.2 | 176.2 |
| 5c | H-Cys(Trt)-ol | 349.2 | 350.2 |
| 6c | H-Glu(OtBu)-ol | 189.2 | 190.2 |
| 7c | H-Gln(Trt)-ol | 374.2 | 375.2 |

TABLE 8-continued

Cleavage of the β-aminoalcohols-resins:

| Cpd num | Compound | MW (g·mol$^{-1}$) | [M + H]$^+$ (Da) |
|---|---|---|---|
| 8c | H-Ile-ol | 117.1 | 118.0 |
| 9c | H-Lys(Boc)-ol | 232.1 | 233.1 |
| 10c | H-Met-ol | 135.1 | 135.9 |
| 11c | H-Ser(tBu)-ol | 147.2 | 148.2 |
| 12c | H-Trp(Boc)-ol | 290.2 | 291.2 |
| 13c | H-Tyr(tBu)-ol | 223.2 | 224.0 |
| 14c | H-Val-ol | 103.1 | 103.9 |
| 15c | Glycinol | 61.1 | 62.0 |
| 16c | H-Phe-ol | 151.1 | 151.9 |

"Cpd num" means "Compound number"

The NMR-$^1$H data are available, in particular in DMSO-d6, but not shown here.

IV. Synthesis of the Di-Isopeptides, i.e. Depsipeptides

By DIC/DMAP Activation

Synthesis scheme 11

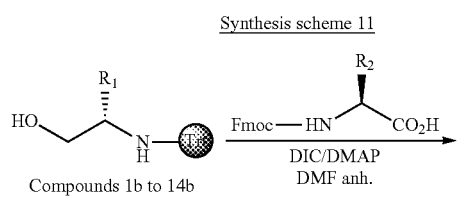

Compounds 1b to 14b

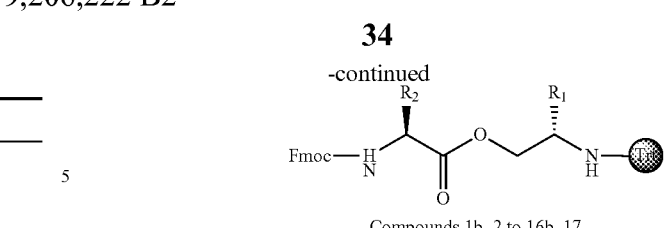

Compounds 1b_2 to 16b_17

Preparation of the Di-Isopeptides Using Dic/Dmap Acylation

DIC (3 eq) and DMAP (0.3 eq) were added to a solution of Fmoc-AA-OH (6 eq relative to resin substitution) in a mixture of anhydrous $CH_2Cl_2$ and DMF (50:50) at 0° C. (3 mL/mmol$^{-1}$). The resulting mixture was stirred with the β-amino alcohol functionalized resin for 6 h at room temperature. This procedure was repeated twice, and then the loading was determined by Fmoc titration.

By using the here-above described process, 98 di-isopeptides were prepared by the DIC/DMAP activation method:

TABLE 9

| DIC/DMAP conditions | |
|---|---|
| Compounds | Qty |
| ⓒ-AA-ol | 25 mg |
| Fmoc-AA-OH | 6 eq |
| DIC | 3 eq |
| DMAP | 0.3 eq |
| DCM/DMF | 1 ml |

"Qty": means "Quantity"

ⓒ: means 2-chlorotrityl resin PS

N.B.: the equivalents were calculated from the initial theoretical substitution level of the 2-chloro-chlorotrityl resin, i.e. 1.55 mmol/g of resin

TABLE 10

Di-isopeptides synthesised by the DIC/DMAP activation method:

| | | 2 Fmoc Arg (Pbf)- OH | 4 Fmoc- Asp (OtBu)- OH | 7 Fmoc- Gln (Trt)- OH | 12 Fmoc- Trp (Boc)- OH | 13 Fmoc- Tyr (tBu)- OH | 14 Fmoc- Val- OH | 17 Fmoc- Pro- OH |
|---|---|---|---|---|---|---|---|---|
| 1b | ⓒAla-ol | 1b_2 | 1b_4 | 1b_7 | 1b_12 | 1b_13 | 1b_14 | 1b_17 |
| 2b | ⓒArg(Pbf)-ol | 2b_2 | 2b_4 | 2b_7 | 2b_12 | 2b_13 | 2b_14 | 2b_17 |
| 3b | ⓒAsn(Trt)-ol | 3b_2 | 3b_4 | 3b_7 | 3b_12 | 3b_13 | 3b_14 | 3b_17 |
| 4b | ⓒAsp(OtBu)-ol | 4b_2 | 4b_4 | 4b_7 | 4b_12 | 4b_13 | 4b_14 | 4b_17 |
| 5b | ⓒCys(Trt)-ol | 5b_2 | 5b_4 | 5b_7 | 5b_12 | 5b_13 | 5b_14 | 5b_17 |
| 6b | ⓒGlu(OtBu)-ol | 6b_2 | 6b_4 | 6b_7 | 6b_12 | 6b_13 | 6b_14 | 6b_17 |
| 7b | ⓒGln(Trt)-ol | 7b_2 | 7b_4 | 7b_7 | 7b_12 | 7b_13 | 7b_14 | 7b_17 |
| 9b | ⓒLys(Boc)-ol | 9b_2 | 9b_4 | 9b_7 | 9b_12 | 9b_13 | 9b_14 | 9b_17 |
| 10b | ⓒMet-ol | 10b_2 | 10b_4 | 10b_7 | 10b_12 | 10b_13 | 10b_14 | 10b_17 |
| 11b | ⓒSer(tBu)-ol | 11b_2 | 11b_4 | 11b_7 | 11b_12 | 11b_13 | 11b_14 | 11b_17 |
| 12b | ⓒTrp(Boc)-ol | 12b_2 | 12b_4 | 12b_7 | 12b_12 | 12b_13 | 12b_14 | 12b_17 |
| 13b | ⓒTyr(tBu)-ol | 13b_2 | 13b_4 | 13b_7 | 13b_12 | 13b_13 | 13b_14 | 13b_17 |
| 15b | ⓒGly-ol | 15b_2 | 15b_4 | 15b_7 | 15b_12 | 15b_13 | 15b_14 | 15b_17 |
| 16b | ⓒPhe-ol | 16b_2 | 16b_4 | 16b_7 | 16b_12 | 16b_13 | 16b_14 | 16b_17 |

ⓒ means 2-chlorotrityl-PS resin

For example: product 1b_2 is: Fmoc-Arg(Pbf)-O—CH$_2$—CH(CH$_3$)—NH-(Trityl resin), product 1b_4 is Fmoc-Asp(OtBu)-O—CH$_2$—CH(CH$_3$)—NH-(Trityl resin), product 16b_2 is Fmoc-Arg(Pbf)-O—CH$_2$—CH(CH$_2$—Ph)—NH-(Trityl resin), etc.

By the Mitsunobu Reaction

Synthesis scheme 12

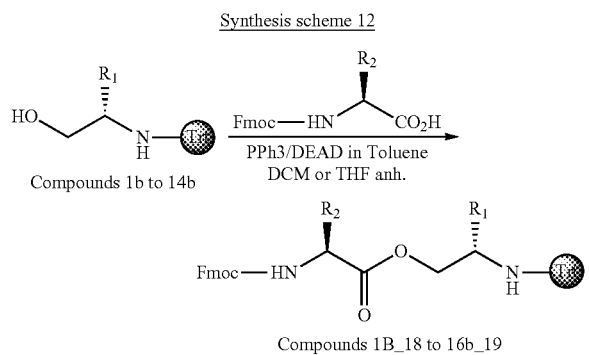

Compounds 1b to 14b

Compounds 1B_18 to 16b_19

Preparation of the Di-Isopeptides Using the Reaction of Mitsunobu

A solution of $PPh_3$ (3 eq) and Fmoc-AA(Trt)-OH (3 eq) in anhydrous THF (AA: Cys) or DCM (AA: His) was added to the resin (20 mL per gram of resin). A 40% solution of DEAD in toluene (3 eq) was then added, and the mixture was stirred for 6 h at room temperature. This procedure was repeated twice.

TABLE 11

| Mitsunobu conditions used | |
|---|---|
| Compounds | Qty |
| ◯-AA-ol | 25 mg |
| Fmoc-AA-OH | 3 eq |
| 40% DEAD in tol. | 3 eq |

TABLE 11-continued

| Mitsunobu conditions used | |
|---|---|
| Compounds | Qty |
| PPh3 | 3 eq |
| DCM | 1 ml |

"Qty": means "Quantity"
◯: means 2-chlorotrityl PS-resin

N.B.: the equivalents were calculated from the initial theoretical substitution level of the 2-chloro-chlorotrityl resin, i.e. 1.55 mmol/g of resin

TABLE 12

| Di-isopeptides synthesised by the Mitsunobu reaction: | | 18 Fmoc-His(Trt)-OH | 19 Fmoc-Cys(Trt)-OH |
|---|---|---|---|
| 1b | ◯-Ala-ol | 1b_18 | 1b_19 |
| 2b | ◯-Arg(Pbf)-ol | 2b_18 | 2b_19 |
| 3b | ◯-Asn(Trt)-ol | 3b_18 | 3b_19 |
| 4b | ◯-Asp(OtBu)-ol | 4b_18 | 4b_19 |
| 5b | ◯-Cys(Trt)-ol | 5b_18 | 5b_19 |
| 6b | ◯-Glu(OtBu)-ol | 6b_18 | 6b_19 |
| 7b | ◯-Gln(Trt)-ol | 7b_18 | 7b_19 |
| 9b | ◯-Lys(Boc)-ol | 9b_18 | 9b_19 |
| 10b | ◯-Met-ol | 10b_18 | 10b_19 |
| 11b | ◯-Ser(tBu)-ol | 11b_18 | 11b_19 |
| 12b | ◯-Trp(Boc)-ol | 12b_18 | 12b_19 |
| 13b | ◯-Tyr(tBu)-ol | 13b_18 | 13b_19 |
| 15b | ◯-Gly-ol | 15b_18 | 15b_19 |
| 16b | ◯-Phe-ol | 16b_18 | 16b_19 |

◯: means 2-chlorotrityl-PS resin

TABLE 13

Examples of di-isopeptides analysis after TFA cleavage with scavengers by LC/MS and determination of the loading:

| | | | | Determination of the loading | | |
|---|---|---|---|---|---|---|
| Cpd num | MW (g·mol$^{-1}$) | HPLC (214 nm) | $[M+H]^+$ (Da) | Experimental (mmol·g$^{-1}$) | Theoritical (mmol·g$^{-1}$) | Yield (%) |
| 1b_17 | 394.2 | 1.65 (95%) | 395.1 | 0.47 | 1.0 | 47 |
| 2b_4 | 497.3 | 1.42 (96%) | 498.3 | 0.37 | 0.70 | 53 |
| 2b_12 | 568.3 | 1.67 (91%) | 569.3 | 0.43 | 0.65 | 66 |
| 3b_7 | 468.2 | 1.43 (94%) | 469.2 | 0.40 | 0.64 | 63 |
| 3b_13 | 503.3 | 1.58 (86%) | 504.2 | 0.45 | 0.71 | 63 |
| 4b_17 | 438.3 | 1.63 (98%) | 439.3 | 0.45 | 0.74 | 61 |
| 5b_2 | 485.2 | 1.58 (82%) | 486.2 | 0.29 | 0.63 | 46 |
| 6b_4 | 470.3 | 1.48 (94%) | 471.2 | 0.46 | 0.84 | 55 |
| 6b_13 | 519.3 | 1.60 (93%) | 519.2 | 0.52 | 0.81 | 64 |
| 7b_7 | 482.3 | 1.43 (92%) | 483.2 | 0.34 | 0.63 | 54 |
| 9b_17 | 451.3 | 1.52 (98%) | 452.3 | 0.53 | 0.86 | 62 |
| 11b_17 | 410.2 | 1.60 (96%) | 411.2 | 0.54 | 0.93 | 58 |
| 12b_2 | 568.3 | 1.73 (83%) | 569.3 | 0.25 | 0.65 | 38 |
| 12b_12 | 598.3 | 1.97 (86%) | 599.3 | 0.32 | 0.71 | 45 |
| 13b_4 | 504.3 | 1.58 (100%) | 505.2 | 0.45 | 0.82 | 55 |
| 13b_13 | 552.3 | 1.68 (100%) | 553.2 | 0.48 | 0.79 | 61 |
| 15b_7 | 411.2 | 1.45 (100%) | 412.2 | 0.41 | 0.79 | 52 |
| 16b_2 | 529.3 | 1.60 (94%) | 530.3 | 0.58 | 0.71 | 82 |
| 16b_17 | 470.3 | 1.88 (96%) | 471.3 | 0.56 | 0.74 | 76 |

"Cpd num" means "Compound number"

TABLE 14

Example of di-isopeptides analysis after TFA cleavage with scavengers by LC/MS and determination of the loading

| Cpd num | MW (g·mol⁻¹) | HPLC (214 nm) | [M + H]⁺ (Da) | Determination of the loading | | Yield (%) |
|---|---|---|---|---|---|---|
| | | | | Loading Exp (mmol·g⁻¹) | Loading Théo (mmol·g⁻¹) | |
| 1b_2 | 705.3 | 1.98 (95%) | 706.2 | 0.53 | 0.78 | 68 |
| 4b_14 | 496.3 | 1.93 (87%) | 497.2 | 0.61 | 0.91 | 67 |
| 7b_14 | 695.3 | 1.23 (94%) | 696.3 | 0.63 | 0.77 | 82 |
| 9b_2 | 862.4 | 2.15 (91%) | 863.4 | 0.37 | 0.68 | 54 |
| 10b_4 | 528.2 | 1.93 (92%) | 529.3 | 0.50 | 0.88 | 57 |
| 10b_12 | 643.3 | 2.20 (93%) | 644.3 | 0.42 | 0.80 | 53 |
| 11b_14 | 468.3 | 1.90 (99%) | 469.2 | 0.73 | 0.93 | 78 |
| 15b_14 | 382.2 | 1.90 (98%) | 383.2 | 0.87 | 1.01 | 86 |

"Cpd num" means "Compound number"

TABLE 15

Example of di-isopeptides analysis after TFE/AcOH/DCM cleavage by LC/MS and determination of the loading

| Cpd num | MW (g·mol⁻¹) | HPLC (214 nm) | [M + H]⁺ (Da) | Determination of the loading | | Yield (%) |
|---|---|---|---|---|---|---|
| | | | | Loading Exp (mmol·g⁻¹) | Loading Théo (mmol·g⁻¹) | |
| 1b_18 | 676.3 | 1.97 (93%) | 677.3 | 0.55 | 0.78 | 71 |
| 10b_18 | 736.3 | 2.02 (86%) | 737.3 | 0.56 | 0.75 | 75 |
| 13b_18 | 824.4 | 2.20 (93%) | 825.4 | 0.46 | 0.70 | 66 |
| 6b_19 | 756.3 | 2.43 (85%) | 757.3 | 0.51 | 0.73 | 70 |
| 15b_19 | 628.2 | 2.23 (96%) | 629.2 | 0.52 | 0.81 | 64 |
| 16b_9 | 718.3 | 2.35 (97%) | 719.3 | 0.56 | 0.75 | 75 |

"Cpd num" means "Compound number"

Optimisation of the Mitsunobu Method

The Mitsunobu method to obtain di-isopeptides was conducted in different solvents to see their impact on the yields, and compared with DIC/DMAP coupling.

TABLE 16

Optimisation of the Mitsunobu method

| Compound | Qty | Loading |
|---|---|---|
| ◎-Ala-ol | 50 mg | |
| Fmoc-His(Trt)-OH | 143 mg | |
| 40% DEAD in toluene | 105 μl | |
| PPh₃ | 60 mg | |
| DCM | 1 ml | 0.55 |
| THF | 1 ml | 0.34 |
| Toluene | 1 ml | 0.01 |

"Qty": means "Quantity"

◎: means 2-chlorotrityl-PS resin

TABLE 17

DIC/DMAP coupling

| Compound | Qty | Loading |
|---|---|---|
| ◎-Ala-ol | 50 mg | |
| Fmoc-His(Trt)-OH | 285 mg | |

TABLE 17-continued

DIC/DMAP coupling

| Compound | Qty | Loading |
|---|---|---|
| DIC | 36 μl | |
| DMAP | 2 mg | |
| DCM/DMF | 1 ml | 0.55 |

"Qty": means "Quantity"

◎: means 2-chlorotrityl-PS resin

The Mitsunobu reaction enabled to obtain the best result in the studied case when DCM was used as a solvent. This was comparable to DIC/DMAP coupling using DCM and DMF as solvent.

N.B.: The quantity of Fmoc-His(Trt)-OH is doubled in comparison with the Mitsunobu conditions, as it is the anhydride which is suspected to react when DIC is used.

Example 3

Preparation of Trichogin GA Iv Using the Pipecolic Linker Resin

The peptide alcohol synthesis strategy of the present invention can also be generalized with the use of other known organic/peptide synthesis resins.

For example a particular resin which was developed in the lab: the pipecolic linker resin, was used to synthesise Trichogin GA IV in the conditions disclosed here above:

Synthesis scheme 13

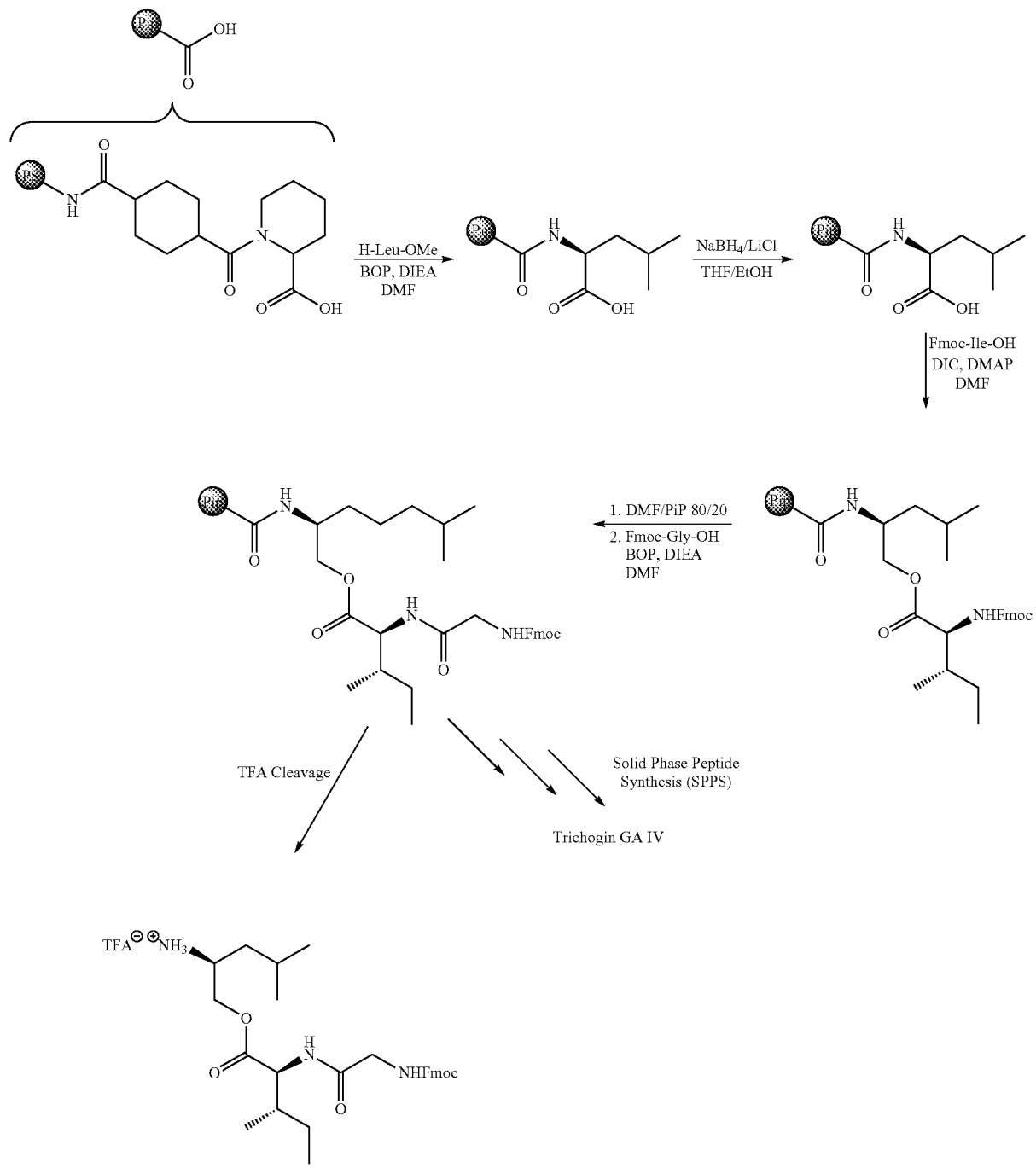

(Trichogin GA IV: H-Aib-Gly-Leu-Aib-Gly-Gly-Leu-Aib-Gly-IlE-Leu-Ol, SEQ ID no 2)

First Amino-Acid Anchoring

The pipecolic linker resin (500 mg, 175 µmol, 0.35 mmol/g) was swollen in DMF for 30 min, and then to the resin was added 8 mL of DMF coupling solution containing BOP (232 mg, 520 µmol, 3 eq), DIEA (203 mg, 274 µl, 1.57 mmol, 9 eq), and H-Leu-OMe.HCl (95 mg, 520 µmol, 3 eq). The resin was gently stirred for 2 hours, washed with DMF (3×), MeOH (2×), DCM (3×) and then dried one night under vacuum.

Reduction of Ester Function

The first amino acid functionalized resin was swollen in 5 mL of THF for 30 min. A first solution containing lithium chloride (95 mg, 2.23 mmol, 12.8 eq) in 10 mL of EtOH and then a second solution of sodium borohydride (85 mg, 2.23 mmol, 12.8 eq) in 5 mL of THF were added to the resin. The resin was stirred at room temperature for 24 h. Excess of borohydride was destroyed by addition of ~2 mL of KHSO$_4$ 1M solution. The resin was then washed with water (3×), MeOH (2×) and DCM (3×).

Esterification of the Leucinol Residue

N,N'-Diisopropylcarbodiimide DIC (84 µL, 68.5 mg, 0.54 mmol, 3 eq.) and DMAP (66 mg, 0.54 mmol, 3 eq) were added to a solution of Fmoc-Ile-OH (382 mg, 1.08 mmol, 6 eq) in a mixture of anhydrous $CH_2Cl_2$ and DMF (50:50) at 0° C. (6 mL). The resulting mixture was stirred during 30 minutes at 0° C. and then stirred with the β-amino-alcohol functionalized resin for 6 h at room temperature. The resin was then washed with DMF (3×), MeOH (2×) and DCM (3×).

Cleavage of the Peptide Off the Resin

The peptides were cleaved off the resin using typical peptide TFA-cleavage conditions, as explained above.

Peptide Chain Elongation

The peptide synthesis was performed using an Fmoc/tBu strategy with BOP/DIEA as coupling reagents. The coupling step was carried out on the resin using $N^\alpha$-Fmoc-amino acid (3 eq) in DMF in the presence of BOP (3 eq) and DIEA (3 eq) for 2 h at room temperature.

The Fmoc deprotection step was performed by treatment with a solution of piperidine (20% v/v in DMF) for 30 min. The deprotection step was repeated twice. After each coupling and deprotection step, the resin was washed with DMF (3×), MeOH (2×) and DCM (3×). The completion of the reaction was checked by the standard Kaiser test and the TNBS test.

Analysis of the Products Obtained

The analysis of the products obtained were done with HPLC, MS, NMR if need-be, and usual analytical techniques used in peptide synthesis or organic synthesis.

Example 4

Preparation of Galanin Using Microwave Peptide Synthesis and the Methodology of the Present Invention Microwave peptide synthesis is now a common process to carry out solid phase peptide synthesis. The present invention also was conducted under these conditions, and proved yet again its great adaptability. Isogalanin was first synthesised using microwave peptide synthesis. IsoGalanine was then cleaved of the resin and transformed into Galanin using either organic conditions (10% TEA in DMF) or aqueous conditions (phosphate buffer).

Isogalanin formula: H-Gly-Trp-Thr-Leu-Asn-Ala-Ala-(D)Trp-Tyr-Leu-Leu-Gly-Pro-His-o-Ala-H (SEQ ID no 4)

N.B.: The "o-Ala-H" on the far right of the molecule, i.e. at the end of chain, is equivalent to: $-O-CH_2-CH(CH_3)NH_2$ Peptide Alcohol Galanin Formula:

H-Gly-Trp-Thr-Leu-Asn-Ala-Ala-(D)Trp-Tyr-Leu-Leu-Gly-Pro-His-Ala-ol (SEQ ID no 5)

Synthesis of Isogalanin

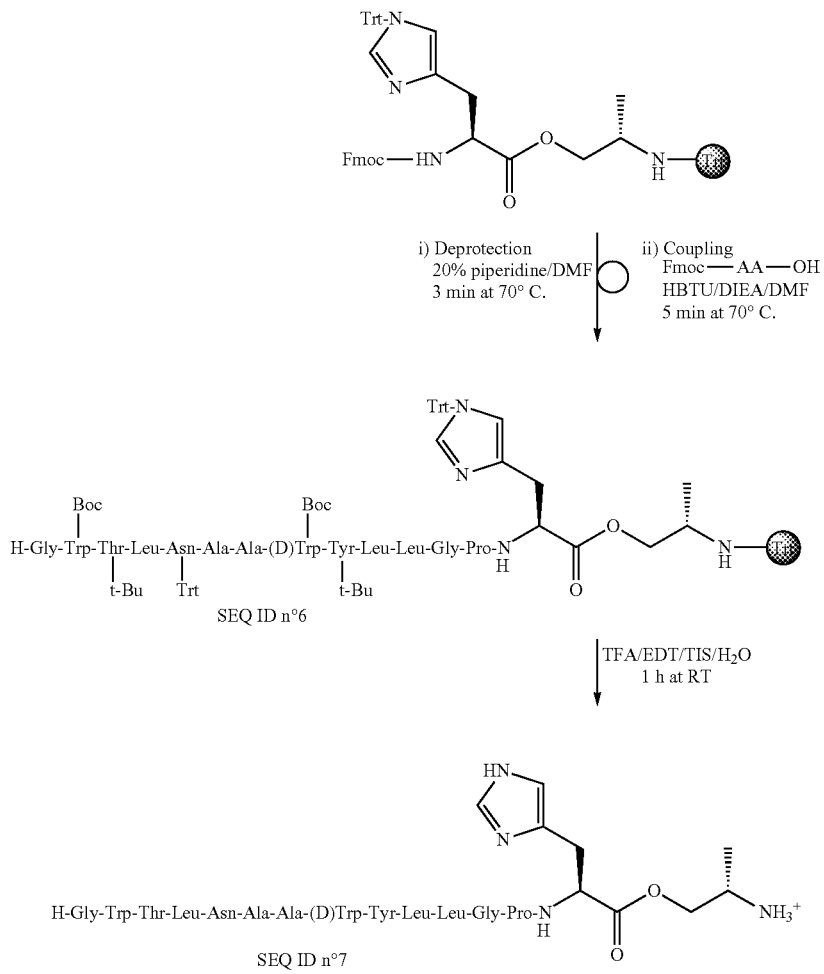

Synthesis scheme 14

The synthesis was done by starting with 200 mg of Fmoc-His(Trt)-o-Ala-H with a loading of 0.55 mmol.g$^{-1}$ (0.1 mmol).

The isopeptides were analysed using HPLC and MS.

TABLE 18

Analysis of the isopeptides

| Sequence | MW (g·mol$^{-1}$) | HPLC (214 nm) | [M + H]$^+$ (Da) | [M + 2H]$^+$/2 (Da) | [M + 3H]$^+$/3 (Da) | Mass (mg) | Yield (%) |
|---|---|---|---|---|---|---|---|
| IsoGalanin | 1654.9 | 1.58 (85%) | # | 828.6 | 552.7 | 180 mg | 85 |

TABLE 19 expected weight

| Mass | 211 mg |
| moles | 0.1 mmol |
| MW + 3 TFA | 1996.9 g·mol-1 |

Synthesis of Galanin

Synthesis scheme 15

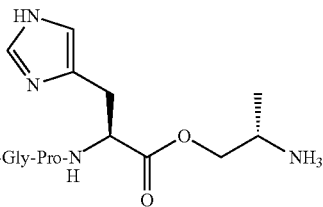

SEQ ID n°7 i) Aqueous media
ii) Organic condition

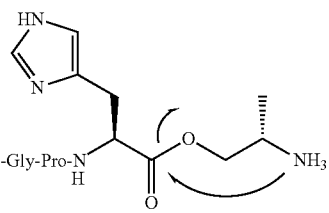

SEQ ID n°4

O—N acyl shift

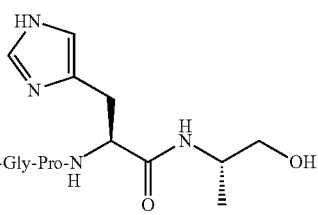

SEQ ID n°5

Isogalanin was transformed into Galanin using either organic conditions (10% TEA in DMF) or aqueous conditions (phosphate buffer).

TABLE 20

Analysis of the peptide alcohols

| Sequence | MW (g·mol$^{-1}$) | HPLC (214 nm) | [M + H]$^+$ (Da) | [M + 2H]$^+$/2 (Da) | [M + 3H]$^+$/3 (Da) | Mass (mg) | Yield (%) |
|---|---|---|---|---|---|---|---|
| Galanin | 1654.9 | 1.58 (86%) | # | 828.6 | 552.7 | 34 | 83 |
| Galanin | 1654.9 | 1.58 (86%) | # | 828.6 | 552.7 | 33 | 81 |

TABLE 21

| expected weight | |
|---|---|
| Mass | 41 mg |
| moles | 0.025 mmol |
| MW | 1654.9 g·mol-1 |

Bibliographic References

E. Benedetti, A. Bavoso, B. Diblasio, V. Pavone, C. Pedone, C. Toniolo, G. M. Bonora, *Proc. Natl. Acad. Sci. USA* 1982, 79, 7951

W. Bauer, U. Briner, W. Doepfner, R. Haller, R. Huguenin, P. Marbach, T. J. Petcher, J. Pless, *Life Sci.* 1982, 31, 1133

J. Alsina, F. Albericio, *Biopolymers* 2003, 71, 454

S. V. Luis et al., *Ind. Eng. Chem. Res.* 2003, 42, 5977-5982

M. S. Whang et al., *J. Ind. Eng. Chem.* 2002, 8, 262-267

J. Tailhades et al., Angew. Chem. 2010, 122, 121-124

SEQUENCE LISTING

```
<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Peptide alcohol : gramicidin A derivative; Leu
      2 and 4 are of the D serie; the terminal COOH is replaced by CH2OH
      on Gly 6

<400> SEQUENCE: 1

Trp Leu Trp Leu Trp Gly
1               5

<210> SEQ ID NO 2
<211> LENGTH: 11
<212> TYPE: PRT
<213> ORGANISM: Artificial
<220> FEATURE:
<223> OTHER INFORMATION: Peptide alcohol : trichogin GA IV derivative;
      the terminal COOH is replaced by CH2OH on Leu11;
<220> FEATURE:
<221> NAME/KEY: misc_feature
<222> LOCATION: (1)..(11)
<223> OTHER INFORMATION: Xaa=2-aminoisobutyric acid

<400> SEQUENCE: 2

Xaa Gly Leu Xaa Gly Gly Leu Xaa Gly Ile Leu
1               5                   10

<210> SEQ ID NO 3
<211> LENGTH: 8
<212> TYPE: PRT
<213> ORGANISM: Artificial
<220> FEATURE:
<223> OTHER INFORMATION: Peptide alcohol : octrotide; Phe1 is (D); Cys 2
      and cys 7 are linked together by a disulphur bridge; Trp 4 is (D);
      the terminal COOH is replaced by CH2OH on Thr 8.

<400> SEQUENCE: 3

Phe Cys Phe Trp Lys Thr Cys Thr
1               5
```

```
<210> SEQ ID NO 4
<211> LENGTH: 15
<212> TYPE: PRT
<213> ORGANISM: Artificial
<220> FEATURE:
<223> OTHER INFORMATION: Peptide alcohol : Isogalanin; Trp 8 is (D); Ala
      15 is inversed in the way O-CH2-CH(CH3)-NH2

<400> SEQUENCE: 4

Gly Trp Thr Leu Asn Ala Ala Trp Tyr Leu Leu Gly Pro His Ala
1               5                   10                  15

<210> SEQ ID NO 5
<211> LENGTH: 15
<212> TYPE: PRT
<213> ORGANISM: Artificial
<220> FEATURE:
<223> OTHER INFORMATION: Peptide alcohol: galanin; Trp 8 is (D); the
      terminal COOH is replaced by CH2OH on Ala 15.

<400> SEQUENCE: 5

Gly Trp Thr Leu Asn Ala Ala Trp Tyr Leu Leu Gly Pro His Ala
1               5                   10                  15

<210> SEQ ID NO 6
<211> LENGTH: 15
<212> TYPE: PRT
<213> ORGANISM: Artificial
<220> FEATURE:
<223> OTHER INFORMATION: Trp2 and Trp8 are substituted by a Boc group;
      Thr 3 and Tyr9 are substituted by a tBu group; Asn5 and His14 are
      substituted by a Trt group; Trp8 is (D); Ala15 is inversed in the
      way O-CH2-CH(CH3)-NH-; Ala15 is linked to Trityl resin via its NH-

<400> SEQUENCE: 6

Gly Trp Thr Leu Asn Ala Ala Trp Tyr Leu Leu Gly Pro His Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Trp8 is of the D series; Ala15 is inversed in
      the following way : O-CH2-CH(CH3)-NH3+; the amine group of Ala1 is
      protonated.

<400> SEQUENCE: 7

Gly Trp Thr Leu Asn Ala Ala Trp Tyr Leu Leu Gly Pro His Ala
1               5                   10                  15
```

The invention claimed is:

1. process for producing the following depsipeptide of formula (VII):

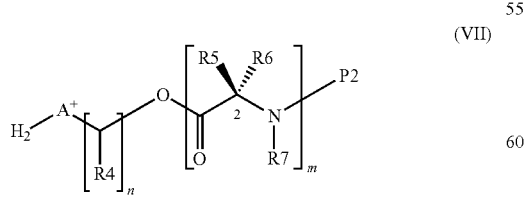

(VII)

wherein, the fragment A represents the amine-Cα(residue)- of an amino acid chosen in the group of natural or unnatural amino acids, n is an integer from 1 to 10;

each R4 is independently selected from the group consisting of a hydrogen atom, a C1-C6 alkyl group, a C2-C6 alkenyl group, a C2-C10 alkynyl group, a (C4-C12) monocyclic or polycyclic saturated hydrocarbonated group, a —(C1-C10 alkyl)-(C4-C12) monocyclic or polycyclic saturated hydrocarbonated group, a (C4-C12) monocyclic or polycyclic unsaturated hydrocarbonated group, and a —(C1-C10 alkyl)-(C4-C12) monocyclic or polycyclic unsaturated hydrocarbonated group, said groups being non substituted or substituted by 1 to 10 fluorine atoms, 1 to 5 —NRR', 1 to 5 SH, 1 to 5OR, 1 to 5 COR, 1 to 5 COOR, 1 to 5 CONRR', 1 to 5 NHCONH2, and/or 1 to 5 NHC(NH)NH2 moieties wherein R and R' are independently from one another selected from the group consisting of a hydrogen atom, a C1-C6 alkyl group, a C2-C6 alkenyl group, a C2-C10 alkynyl group, a (C4-C12) monocyclic or polycyclic saturated hydrocarbonated group, a —(C1-C10 alkyl)-(C4-C12) monocyclic or polycyclic saturated hydrocarbonated group, a (C4-C12) monocyclic or polycyclic unsaturated hydrocarbonated group, and a —(C1-C10 alkyl)-(C4-C12) monocyclic or polycyclic unsaturated hydrocarbonated group;

m is an integer from 1 to 100, wherein when m is greater than 1, the bracketed amino acid residue is the same or different;

each R5 and R6 is independently selected from the group consisting of a hydrogen atom, a fluorine atom, a C1-C20 alkyl group, a C2-C10 alkenyl group, a C2-C10 alkynyl group, a (C4-C12) monocyclic or polycyclic hydrocarbonated group, a —(C1-C10 alkyl)-(C4-C12) monocyclic or polycyclic hydrocarbonated group, a —(C1-C10 alkyl)-S-(C1-C10 alkyl) group, a —(C1-C10 alkyl)-indol-2-yl group, and a -(C1-C10 alkyl)-imidazolyl group, said groups being non substituted or substituted by 1 to 10 fluorine atoms, 1 to 5 —NRR', 1 to 5 SH, 1 to 5 OR, 1 to 5 COR, 1 to 5 COOR, 1 to 5 CONRR', 1 to 5 NHCONH2, and/or 1 to 5 NHC(NH)NH2 moieties wherein R and R' are independently selected from the group consisting of a hydrogen atom, a C1-C6 alkyl group, a C2-C6 alkenyl group, a C2-C10 alkynyl group, a (C4-C12) monocyclic or polycyclic saturated hydrocarbonated group, a —(C1-C10 alkyl)-(C4-C12) monocyclic or polycyclic saturated hydrocarbonated group, a (C4-C12) monocyclic or polycyclic unsaturated hydrocarbonated group, and a —(C1-C10 alkyl)-(C4-C12) monocyclic or polycyclic unsaturated hydrocarbonated group, wherein the NH2, NH, COOH, SH and OH functions of these groups are optionally protected by one or several identical or different O-protecting and/or N-protecting and/or S-protecting groups or atoms;

each R7 is independently selected from the group consisting of a hydrogen atom, a C1-C6 alkyl group, a C2-C6 alkenyl group, a C2-C6 alkynyl group, a (C4-C12) monocyclic or polycyclic saturated hydrocarbonated group, a —(C1C10 alkyl)-(C4-C12) monocyclic or polycyclic saturated hydrocarbonated group, a (C4-C12) monocyclic or polycyclic unsaturated hydrocarbonated group, a —(C1-C10 alkyl)-(C4-C12) monocyclic or polycyclic unsaturated hydrocarbonated group, and a CO—R group, wherein R represents a hydrogen, a C1-C6 alkyl group, a C2-C6 alkenyl group, a C2-C10 alkynyl group, a (C4-C12) monocyclic or polycyclic saturated hydrocarbonated group, a —(C1-C10 alkyl)-(C4C12) monocyclic or polycyclic saturated hydrocarbonated group, a (C4-C12) monocyclic or polycyclic unsaturated hydrocarbonated group, or a —(C1-C10 alkyl)-(C4-C12) monocyclic or polycyclic unsaturated hydrocarbonated group;

R7 and R5, and/or R7 and R6 can form together with the atoms which carry them a monocyclic or polycyclic moiety wherein each ring is a 3- to 10-membered hydrocarbonated ring, saturated or unsaturated, the number of rings being comprised between 1 and 5, non-substituted or substituted by 1 to 10 fluorine atoms, 1 to 5 —NRR', 1 to 5 SH, 1 to 5 OR, 1 to 5COR, 1 to 5 COOR, 1 to 5 CONRR', 1 to 5 NHCONH2, and/or 1 to 5 NHC(NH)NH2 moieties wherein R and R' are independently selected from the group consisting of a hydrogen atom, a C1-C6 alkyl group, a C2-C6 alkenyl group, a C2-C10 alkynyl group, a (C4-C12) monocyclic or polycyclic saturated hydrocarbonated group, a —(C1-C10 alkyl)-(C4-C12) monocyclic or polycyclic saturated hydrocarbonated group, a (C4-C12) monocyclic or polycyclic unsaturated hydrocarbonated group, and a —(C1-C10 alkyl)-(C4-C12) monocyclic or polycyclic unsaturated hydrocarbonated group, wherein the NH2, NH, COOH, SH and OH functions of these groups are optionally protected by one or several identical or different O-protecting and/or N-protecting and/or S-protecting groups or atoms;

P2 represents a hydrogen atom or an N-protecting group; and the α-carbon of each bracketed amino acid residue, marked 2, can independently have an R or S configuration if said α-carbon is an asymmetrical carbon, the process comprises:

a) providing a solid phase amino alcohol of formula (I):

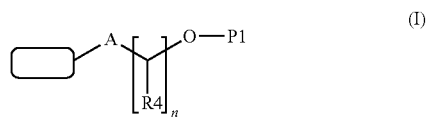

wherein P1 represents an O-protecting group and □ represents a solid support appropriate for peptide synthesis;

b) removing the O-protecting group P1 from the solid phase amino alcohol of formula (I);

c) coupling a conveniently protected amino acid of formula (VI):

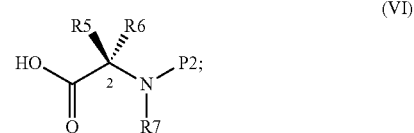

d) removing the N-protecting group P2;

e) repeating steps c) and d) 0 to 99 times;

f) removing the solid support by acidic cleavage to yield the depsipeptide of formula (VII).

2. A method for the synthesis of the following peptide alcohol of formula (VIII):

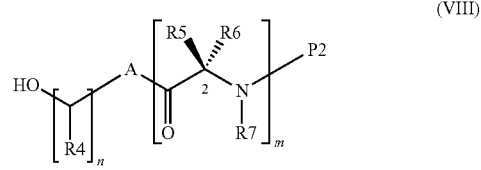

wherein the fragment A represents the amine-C$_\alpha$(residue)- of an amino acid chosen in the group of natural or unnatural amino acids, n is an integer from 1 to 10, each R4 is independently selected from the group consisting of a hydrogen atom, a $C_1$-$C_6$ Alkyl group, a $C_2$-$C_6$ alkenyl group $C_2$-$C_{10}$ alkynyl group, $C_4$-$C_{12}$ monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, and a —($C_1$-$C_{10}$ alkyl)-($C_4$-$C_{12}$) monocyclic or polycyclic unsaturated hydrocarbonated group, said groups being non substituted or substituted by 1 to 10 fluorine atoms, 1 to 5 -NRR', 1to 5 SH, 1 to 5 OR, 1 to 5 COR, 1 to 5 COOR, 1 to 5 CONRR', 1 to 5 NHCONH$_2$, and/or 1 to 5NHC(NH)NH$_2$ moieties wherein R and R' are independently from one another selected from the group consisting of a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$alkyl)-($C_4$-$C_{12}$) monocyclic or polycyclic saturated hydrocarbonated group, a ($C_4$-$C_{12}$) monocyclic or polycyclic unsaturated hydrocarbonated group, and a —($C_1$-$C_1$)-($C_4$-$C_{12}$) monocyclic or polycyclic unsaturated hydrocarbonated group, and m is an integer from 1 to 100, each R5 and R6 are independently chosen from the group consisting of a hydrogen atom, a fluorine atom, a $C_1$-$C_{20}$ alkyl group, a $C_2$-$C_{10}$ alkenyl group, a $C_2$-$C_{10}$ alkynyl group, a ($C_4$-$C_{12}$) monocyclic or polycyclic hydrocarbonated group, a —($C_1$-$C_{10}$ alkyl)-($C_4$-$C_{12}$) monocyclic or polycyclic hydrocarbonated group, a —($C_1$-$C_{10}$ alkyl)-S-($C_1$-$C_{10}$ alkyl) group, a —($C_1$-$C_{10}$ alkyl) indol-2-yl group, and -(C_-$C_{10}$alkyl) group, said groups being non substituted or substituted by 1 to 10 fluorine atoms, 1 to 5 —NRR', 1 to 5 SH, 1 to 5 OR, 1 to 5 COR, 1 to 5COOR, 1 to 5 CONRR', 1 to 5 NHCONH$_2$, and/or 1 to 5 NHC(NH)NH$_2$ moieties wherein R and R' are independently from one another chosen from the group consisting of a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group ($C_4$-$C_{12}$ )monocyclic or poltcyclic unsaturated hydrocarbonated group, and a —($C_1$-$C_{10}$ alkyl)-($C_4$-$C_{12}$) monocyclic or polycyclic unsaturated hydrocarbonated group, each R7 are independently chosen from the group consisting of a hydrogen atom, a $C_1$-$C_6$ alkyl group, a $C_2$-$C_6$ alkenyl group, a $C_2$-$C_6$ alkynyl group, a ($C_4$-$C_{12}$ monocyclic or polycyclic saturated hydrocarbonated group, a —($C_1$-$C_{10\ alkyl)-(C4}$-$C_{12}$ ) monocyclic or polycyclic saturated hydrocarbonated group, a ($C_4$-$C_{12}$) monocyclic or polycyclic unsaturated hydrocarbonated group, a —($C_1$-$C_{10}$ alkyl)-($C_4$-$C_{12}$) monocyclic or polycyclic unsaturated hydrocarbonated group, and a CO-R group, wherein R represents a hydrogen, a $C_1$-$C_6$alklyn group, a $C_2$-$C_6$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated hydrocarbonated group, a ($C_4$-$C_{12}$) monocyclic or polycyclic unsaturated hydrocarbonated group, or a —($C_1$-$C_{10}$ alkyl)-($C_4$-$C_{12}$) monocyclic or polycyclic unsaturated hydrocarbonated group, or R7 and R5, and/or R7 and R6 can form together with the atoms which carry them a monocyclic or polycyclic moiety wherein each ring is a 3- to 10-membered hydrocarbonated ring, saturated or unsaturated, the number of rings being comprised between 1 and 5, non substituted or substituted by 1 to 10 fluorine atoms , 1 to 5 —NRR', 1 to 5 SH, 1 to 5 OR, 1 to 5COR, 1 to 5 COOR, 1 to 5 CONRR', 1 to 5 NHCONH$_2$, and/or 1 to 5 NHC(NH)NH$_2$ moieties wherein R and R' are independently from one another chosen from the group consisting of a hydrogen atom, a $C_1$-$C_6$ alkyl group, a $C_2$-$C_6$ alkenyl group, a $C_2$-$C_{10}$ alkynyl group, a ($C_4$-$C_{12}$) monocyclic or polycyclic saturated hydrocarbonated group, a —($C_1$-$C_{10}$ alkyl)-($C_4$-$C_{12}$) monocyclic or polycyclic saturated group, a ($C_4$-$C_{12}$) monocyclic or polycyclic unsaturated hydrocarbonated group, and a —($C_1$-$C_{10}$ alkyl)-($C_4$-$C_{12}$) monocyclic or polycyclic unsaturated hydrocarbonated group, P2 represents a hydrogen atom or an N-protecting group, and the α-carbon of each bracketed amino acid residue, marked 2, can independently have an R or S configuration if said a-carbon is an asymmetrical carbon, the method comprising:

the process for producing the depsipeptide of formula (VII) of claim 1; and a step (g)of O-N acyl shift of the depsipeptide of formula (VII), using basic conditions or buffered conditions.

3. The method according to claim 2 wherein dimethylformamide and piperidine or an aqueous phosphate buffer are used in step (g).

* * * * *